(12) United States Patent
Todorov et al.

(10) Patent No.: US 11,445,919 B2
(45) Date of Patent: Sep. 20, 2022

(54) SYSTEMS FOR ASSESSING AND OPTIMIZING MUSCULAR PERFORMANCE

(71) Applicant: SOMAXIS INCORPORATED, San Jose, CA (US)

(72) Inventors: Alex Todorov, Santa Clara, CA (US); Alexander B Grey, Campbell, CA (US)

(73) Assignee: SOMAXIS INCORPORATED, San Jose, CA (US)

(*) Notice: Subject to any disclaimer, the term of this patent is extended or adjusted under 35 U.S.C. 154(b) by 1852 days.

(21) Appl. No.: 15/083,252

(22) Filed: Mar. 28, 2016

(65) Prior Publication Data
US 2016/0206225 A1 Jul. 21, 2016

Related U.S. Application Data

(63) Continuation of application No. 13/239,033, filed on Sep. 21, 2011, now Pat. No. 9,295,424.
(Continued)

(51) Int. Cl.
*A61B 5/05* (2021.01)
*A61B 5/0205* (2006.01)
(Continued)

(52) U.S. Cl.
CPC .......... *A61B 5/0205* (2013.01); *A61B 5/0006* (2013.01); *A61B 5/112* (2013.01);
(Continued)

(58) Field of Classification Search
CPC ......... A61B 5/296; A61B 5/282; A61B 5/389; A61B 5/0006; A61B 5/0024; A61B 5/6833; A61B 5/0205; A61B 5/316; A61B 5/318; A61B 5/25; A61B 5/259; A61B 2562/0219; A61B 5/24; A61B 5/0022; A61B 2562/164; A61B 5/0245;
(Continued)

(56) References Cited

U.S. PATENT DOCUMENTS 6,434,410 B1 * 8/2002 Cordero .................. A61B 5/282
600/396
6,440,067 B1 * 8/2002 DeLuca ................... A61B 5/389
600/300
(Continued)

*Primary Examiner* — Joseph A Stoklosa
*Assistant Examiner* — Brian M Antiskay
(74) *Attorney, Agent, or Firm* — David A. Jones; Alpine IP

(57) ABSTRACT

Monitoring muscle data can include one or more fully flexible sensor patches having sensor modules configured to sense muscle data, data processing modules, transmitter modules configured to transmit the muscle data, and a microcontroller configured to control the modules on one patch side and an adhesive layer on the other patch side; a wearable mobile hub having one or more of a receiver, transmitter, and/or transceiver module configured to be operably coupled with the one or more sensor patches so as to receive muscle data therefrom and a muscle data processing unit configured to process the received muscle data, and one or more user feedback interfaces to provide processed muscle data to the one or more user feedback interfaces; and a base station configured for receiving, storing, and analyzing the muscle data for one subject received from the mobile hub in comparison with one or more other subjects.

2 Claims, 16 Drawing Sheets

Related U.S. Application Data

(60) Provisional application No. 61/514,148, filed on Aug. 2, 2011, provisional application No. 61/385,049, filed on Sep. 21, 2010, provisional application No. 61/385,038, filed on Sep. 21, 2010, provisional application No. 61/385,046, filed on Sep. 21, 2010, provisional application No. 61/385,051, filed on Sep. 21, 2010, provisional application No. 61/385,053, filed on Sep. 21, 2010, provisional application No. 61/385,048, filed on Sep. 21, 2010.

(51) Int. Cl.

| | |
|---|---|
| *A61B 5/22* | (2006.01) |
| *A61B 5/00* | (2006.01) |
| *A61B 5/11* | (2006.01) |
| *G16H 50/20* | (2018.01) |
| *G16H 20/30* | (2018.01) |
| *A61B 5/25* | (2021.01) |
| *A61B 5/296* | (2021.01) |
| *A61B 5/316* | (2021.01) |
| *A61B 5/318* | (2021.01) |
| *A61B 5/389* | (2021.01) |
| *G16H 50/50* | (2018.01) |
| *G16H 20/10* | (2018.01) |
| *G16H 20/40* | (2018.01) |
| *A61B 5/01* | (2006.01) |

(52) U.S. Cl.
CPC .............. *A61B 5/222* (2013.01); *A61B 5/224* (2013.01); *A61B 5/25* (2021.01); *A61B 5/296* (2021.01); *A61B 5/316* (2021.01); *A61B 5/318* (2021.01); *A61B 5/389* (2021.01); *A61B 5/486* (2013.01); *A61B 5/4866* (2013.01); *A61B 5/6801* (2013.01); *A61B 5/6833* (2013.01); *A61B 5/725* (2013.01); *A61B 5/7235* (2013.01); *A61B 5/7246* (2013.01); *A61B 5/7275* (2013.01); *A61B 5/746* (2013.01); *G16H 20/10* (2018.01); *G16H 20/30* (2018.01); *G16H 20/40* (2018.01); *G16H 50/20* (2018.01); *G16H 50/50* (2018.01); *A61B 5/01* (2013.01); *A61B 2503/10* (2013.01); *A61B 2560/0223* (2013.01); *A61B 2560/0238* (2013.01); *A61B 2560/0412* (2013.01); *A61B 2562/164* (2013.01)

(58) Field of Classification Search
CPC .......... A61B 2560/0412; A61B 5/1118; A61B 5/6804; A61B 5/11; A61B 5/0002; A61B 5/6831; A61B 5/02438; A61B 5/6824; A61B 2562/04
USPC .................. 600/372, 382–393, 508–509
See application file for complete search history.

(56) References Cited

U.S. PATENT DOCUMENTS

| | | | |
|---|---|---|---|
| 8,666,471 B2 * | 3/2014 | Rogers ................ | A61B 5/6867 607/116 |
| 9,439,599 B2 * | 9/2016 | Thompson ............ | G16H 40/67 |
| 2002/0180605 A1 * | 12/2002 | Ozguz ................ | H01L 21/6836 340/573.1 |
| 2003/0109905 A1 * | 6/2003 | Mok .................... | A61B 5/0002 607/60 |
| 2007/0167848 A1 * | 7/2007 | Kuo ...................... | H01C 10/32 600/509 |
| 2007/0270678 A1 * | 11/2007 | Fadem .................... | A61B 5/30 600/372 |
| 2008/0275327 A1 * | 11/2008 | Faarbaek ........... | A61B 5/68335 600/382 |
| 2009/0292194 A1 * | 11/2009 | Libbus ............... | A61B 5/02438 600/391 |
| 2009/0299212 A1 * | 12/2009 | Principe ................ | G16Z 99/00 600/547 |
| 2011/0009729 A1 * | 1/2011 | Shin ...................... | A61B 5/303 600/391 |
| 2011/0077497 A1 * | 3/2011 | Oster .................... | A61B 5/274 600/372 |
| 2011/0279963 A1 * | 11/2011 | Kumar ............... | A61B 5/68335 361/679.31 |

\* cited by examiner

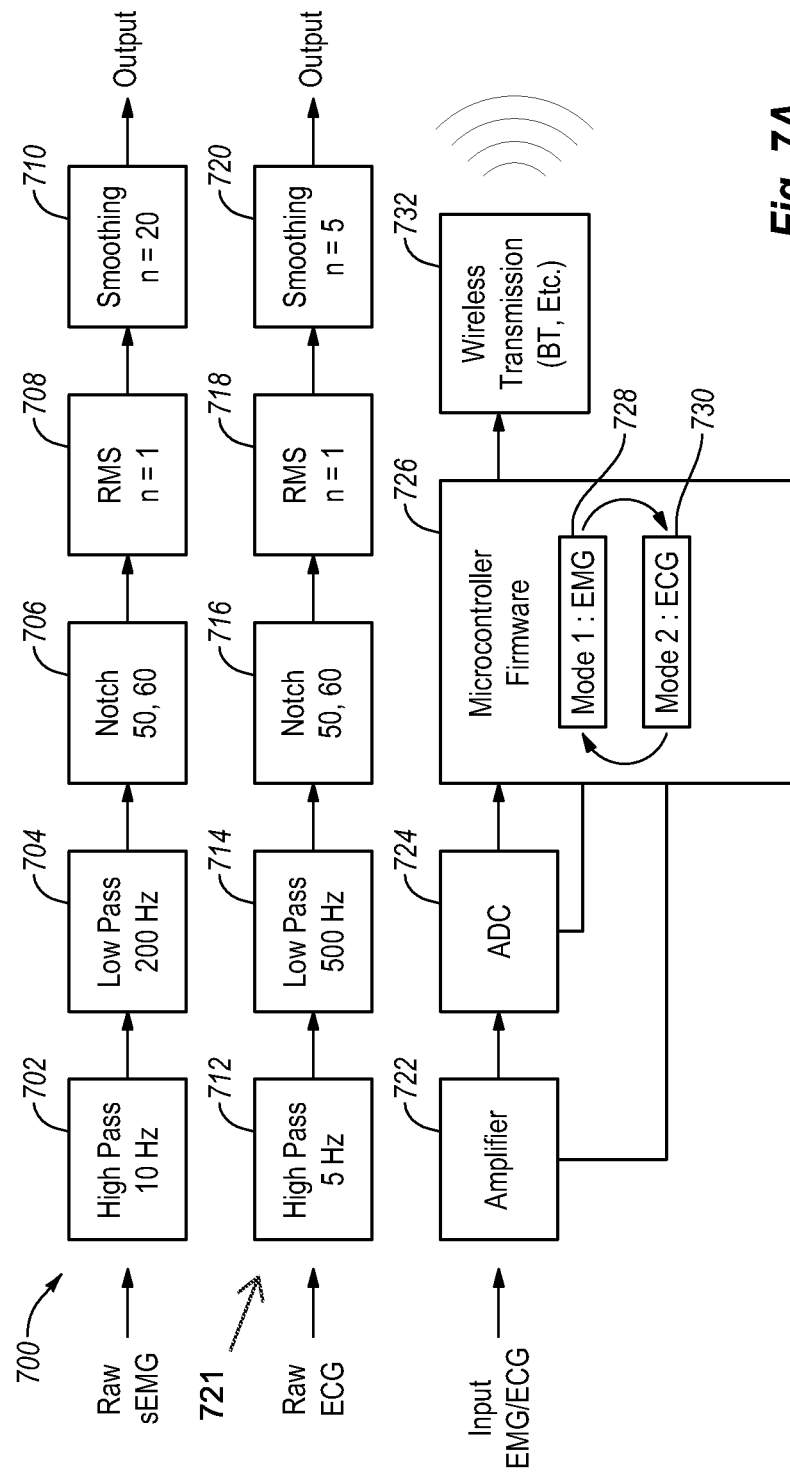
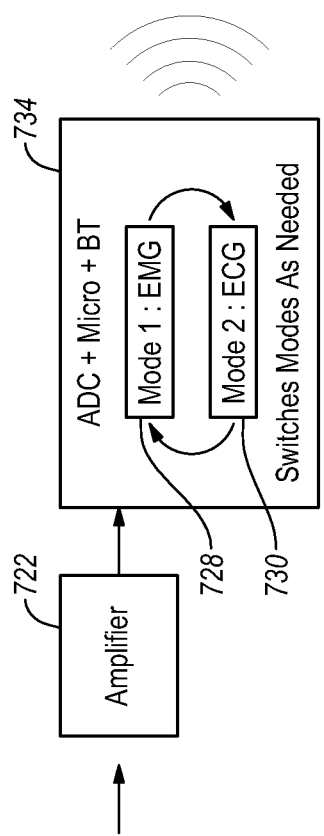
Fig. 7A
Fig. 7B

SYSTEMS FOR ASSESSING AND OPTIMIZING MUSCULAR PERFORMANCE

CROSS-REFERENCE TO RELATED APPLICATIONS

This patent application is a continuation of U.S. Ser. No. 13/239,033 filed Sep. 21, 2011, which claims the benefit of U.S. Provisional Application Nos. 61/385,046, 61/385,038, 61/385,048, 61/385,049, 61/385,051, and 61/385,053 all of which were filed on Sep. 21, 2010. U.S. Ser. No. 13/239,033 filed Sep. 21, 2011 claims the benefit of U.S. Provisional Application No. 61/514,148, filed Aug. 2, 2011. All of the aforementioned patent applications are incorporated herein by specific reference in their entirety.

BACKGROUND OF THE INVENTION

Electrophysiological modalities related to muscles and their activation and performance can be measured by devices configured to sense electrical information, such as skeletal muscle monitors (e.g., electromyography) or cardiac muscle monitors (e.g., electrocardiography). The electrophysiology modalities can be measured with: electrocardiography (ECG), electroencephalography (EEG), electrocorticography (ECoG), electromyography (EMG), electrooculography (EOG), electroretinography (ERG), electroantennography (EAG), and audiology. There are similarities and critical differences between these electrophysiology modalities; however, it is important to note that the electrophysiology modalities can be quite different from each other. For example, a galvanic skin response (GSR) system has unique characteristics such as amplification factors, filters, and others that are not present in an electrocardiography (ECG) system. As such, sensors for the different electrophysiology modalities can be substantially different from each other, and cross-compatibility usually is not available or an option. That is, a sensor for one electrophysiology modality is not useful for a different modality.

Multi-modal electrophysiology systems do exist, but it is important to note that these systems tend to become significantly less useful for specific modalities. For example, a user may find a product which measures ECG, EMG, EEG, skin temperature, EOG, skin conductance, and a handful of other modalities. However, for a "stress test" which involves high-impact activity for an extended period of time (e.g., ECG and EMG are primary modalities), these systems become impractical to use. The multi-modal device often results in a device that is too big for many purposes, such as wearing during exercise, and it is nearly impossible to reduce the multi-modal device to a size small enough so that the dimensions and mass of the device are suitable for being worn. Frequently, the transmitter is included in a housing separated from the sensor housing, and may be overly bulky for wearing. As a result, a user may need to wear a backpack or a belt pack to hold the one of the necessary components.

sEMG and ECG are two modalities that are capable of measuring, filtering, interpreting, and displaying electrical data from muscles. First generation sEMG or ECG systems were completely wired and included sensors that were applied to the skin of the user, where two sensors were required per muscle group being monitored such that each pair of sensors generates one channel of data. The systems also include one body reference sensor commonly referred to as a ground sensor. The body reference sensor could be common to multiple channels. The first generation hardware did not typically have feedback through a computer base station; however, feedback was hardware-generated through boxes with arrays of LEDs that would show instantaneous rectified sEMG amplitude. Alarms for audio feedback were set manually as well. Total range of the user was determined by the length of the cable which connected the sensors to the base station. The base station was provided to perform computing of the data and any data analysis.

Second generation systems include partially wireless having a primary advance of a telemetric and/or wireless link between the user and the base station. The base station in this generation is usually a personal computer that was configured to receive and analyze data received from sensors applied to the skin. The sensors can be attached to cables, which ran back to a portable box configured for data amplification and included hardware filters and a wireless transmitter. The wireless component allows the user to be able to walk away from the base station at a distance of about 50 feet (e.g., line-of-sight) or less. Feedback to the user could be in real time, such as by live graphs or audio of the muscle data (e.g., rectified amplitude for sEMG).

Third generation technologies include integrated sensor/transmitters which typically are one channel each, and transmit data from the surface of the skin, to which they are adhesively attached, to a base station (e.g., a personal computer). Typically, two operating modes exist: (1) the user is interested in getting live feedback, and for this they have to be within visual range of the base station on which the feedback is being displayed; or (2) the user is out of range of the base station such that data is automatically saved internally to the device worn by the use. The third generation allowed users to exercise remotely from the base station, and synchronize their data with the base station when in range.

BRIEF SUMMARY OF THE INVENTION

These and other limitations are overcome by embodiments of the invention which relate to systems and methods for This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

Additional features and advantages of the invention will be set forth in the description which follows, and in part will be obvious from the description, or may be learned by the practice of the invention. The features and advantages of the invention may be realized and obtained by means of the instruments and combinations particularly pointed out in the appended claims. These and other features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

Figure The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 7A includes a schematic representation of components of an embodiment of a base station of a sensor system;

FIG. 7B includes a schematic representation of an alternative embodiment of a microcontroller of a base station of a sensor system;

Figure 1:
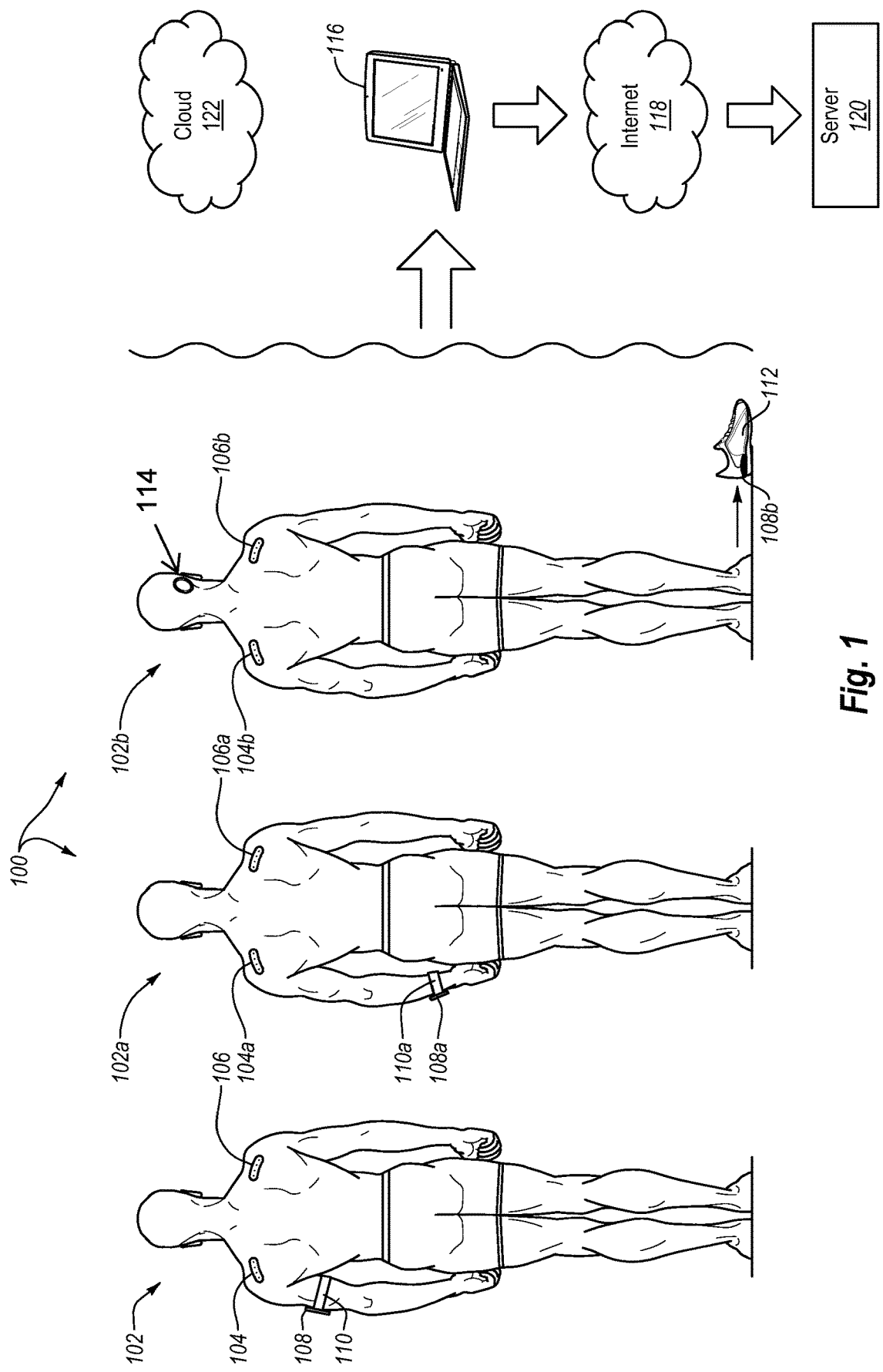
FIG. 1 includes a schematic representation of different embodiments of a sensor system in communication with a computing system, where the communication can be over a network.

arranged in accordance with at least one of the embodiments described herein, and which arrangement may be modified in accordance with the disclosure provided herein by one of ordinary skill in the art.

DETAILED DESCRIPTION OF THE PREFERRED EMBODIMENTS

Embodiments In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting.

Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to muscle sensor patches, a sensor system having the muscle sensor patches, and methods of using the same for acquiring muscle data. The muscle data may be sEMG data, but may also include other types of data related to muscles. Also, the muscle sensor patches can include other modules that may obtain relevant data about the subject wearing the patches, which data can be relevant to various muscle activities, exercise, or athletics.

Prior muscle sensors only include sEMG sensor modules, and only allow for live feedback to the user within a limited range of a base station (50 feet). However, now the present invention provides a muscle sensor system that is configured to provide sophisticated live feedback at any physical location the user chooses. There are no range restrictions with regard to a base station of the system. The advancements in muscle sensor systems can be obtained with the inclusion of a mobile hub to the sensor system, which represents an improvement over the existing muscle sensor configurations. The mobile hub is a fully functional computing device having hardware and/or software suitable for receiving muscle data from sensor patches, storing the data, processing the data, providing the processed data to the subject wearing the patches and mobile hub via user interfaces, and to transmit the data to a base station. The base station can be configured as is known in the art. The sensor patch and mobile hub provide significant improvements in usability and data processing and interfacing with the user in real time or on the fly. Additionally, the inventive muscle sensor system can include a reference database, running on one or more servers (e.g., cloud) that is in communication with the mobile hub and/or base station. The server can receive data from the user and provide data from the database of two or more users. The inventive muscle sensor system may be able to communicate with the one or more servers to acquire information from the database in real time or on the fly.

In one embodiment, the inventive muscle sensor system can include a transceiver, mobile receiver, and a base station, and optionally one or more servers running a reference database which may be located remotely (e.g., internet, cloud). The muscle sensor system may be able to access the database by mobile communications or wireless data communications or through the internet, or any other manner for accessing a remote computing device wirelessly. The embodiment including the one or more servers can include four or more microprocessors for a single channel of data. This is a significant upgrade in computing and processing power over prior systems that only included two units having processors. The additional processors greatly improve the computing and data processing abilities to improve the ability of a user to interface with their own muscle data and metrics associated therewith. Additionally, the inclusion of data communication components that can operate over mobile communication channels or internet provides a substantially unlimited range for which all of the components of the muscle sensor system can operate, interact, and exchange data.

The muscle sensor patches can be adapted to be mounted to the skin, which can reside on the skin for a short or long duration depending on the user. The user can remove the muscle sensor patch once it becomes overly worn or begins to disassociate from the skin. The muscle sensor patches can include a skin-adhering surface that provides for one or more sensor elements to be operably coupled to the skin and thereby the muscles so as to be capable of receiving muscle data. Each sensor element can be adapted as a one-channel sEMG/ECG, and can be placed on the surface of the skin when the patch is worn by a user. The sensor element can include single conductive area sEMG/ECG sensors.

The skin-adhering surface of the muscle sensor patch can include an area that is conductive and non-adhesive, which can be configured similarly as an ultrasound gel that is either fluidic or non-fluidic. Alternatively, the area can be conductive and less adhesive than a common pressure sensitive adhesive patch. This conductive area that is non-adhesive or less adhesive can be located within the perimeter of the skin-adhering surface, with a border of varying dimension. The border or outer area around the conductive area is completely non-conductive. The border can also include an adhesive that has significant tact to stick to skin. Pressure sensitive adhesives are a good example of the adhesive quality provided by the border. The non-conductive, adhesive border may also have one or more strips that extend partially or all the way across the skin-adhering surface, such as from one side of the border to an internal region or all the way from one side of the border to another side of the border. The skin-adhering surface can include one, two, three, four, or more conductive areas surrounded by adhesive areas. Alternatively, the sensor is both conductive and adhesive for the entirety of the skin-adhering surface, or majority thereof.

When a large portion of the skin-adhering surface is more conducive and less adhesive, the adherence can decrease over time, or be more susceptible to peeling or falling off of the skin in situations that put more stress on the sensors (i.e., movement during a muscle activity or athletics). Additionally, when a user sweats or secretes oil from their skin, it reduces the conductivity of the sensor and allows for ions to build up in the contact area, which reduces the ability to obtain or measure electrophysiological data. When this occurs, the user can dispose of the patch and use a new patch. Alternatively, the user can peel the skin-contacting layer from the patch to reveal a fresh skin-contacting surface underneath with fresh adhesive.

The patches are prepared from multiple layers of materials that are bound together in thin bandages adapted to improve wearability. The patches can include the components of the sensor/transceiver embedded in or between the one or more layers of materials while maintaining flexibility in all three dimensions. Alternatively, the layers can be electronically coupled with the external most layer having the sensor modules. The different layers of the patch are prepared from flexible materials, and the patch is assembled without any structural members that would inhibit flexibility in three dimensions. The materials are suitable to maintain contact with the skin as it stretches.

In an alternative embodiment, the patches can be provided as a kit having one skin patch substrate with the sensor modules and associated electronics and one adhesive substrate. The adhesive substrate can be adhesive on both sides, and may or may not include peelable protective layers, which can be removed prior to adhering to the sensor module skin patch substrate and to the skin of a user. The used adhesive substrate can be removed from the sensor module substrate and discarded, and a new adhesive substrate can be applied.

The patches can be prepared to have an area on the skin-adhering surface that does not include adhesive so that it can move with respect to the skin during a muscle activity. The lack of adhesive combined with the flexibility of the patch improves the wearability and allows the sensor portion to float with the skin as accommodated by the flexible patch. A rigid or semi-rigid gelatinous sensor contact area can maintain contact with the skin while also allowing the skin to stretch and flex. The gelatinous material maintains contact and adjusts contouring with the skin surface to maintain contact over the entire same area during movement.

The sensor patches can include electrophysiology sensors that provide data signals for activation and function of muscles. The signal can be detected at the surface of the skin by conductive sensors, such as two or three sensors, depending on the application. The signal from the sensors can be amplified, and may be processed through hardware filters. Filters are always needed for the raw signal; however, the filters may be in hardware only, firmware only, or in a combination of both hardware and firmware. Typically, filters utilized are high pass, low pass, band pass, and/or a notch filter around 50 or 60 Hz. The values used for the filters can depend on the application. For example, ECG often passes frequency information in the range of approximately 5 Hz-40 Hz. EMG often passes frequency information in the range of approximately 10 Hz-500 Hz. After hardware filters, the signal can be digitized through an analog to digital converter (ADC). The ADC may or may not be integrated into the microcontroller. The microcontroller has a number of functions, such as to initialize and control the operation of the peripherals of the device as necessary. The microcontroller may then take the data and perform additional calculations on it, depending on whether raw data or post-filtered data or metrics are transmitted from the device. If raw data is transmitted, then the post-filtered data is sent directly to the radio module (e.g., Bluetooth, Zigbee, ANT+, proprietary RF schemes, etc.). If raw data transmission is not practical or desirable, then the microcontroller can run algorithms that produce meaningful metrics of interest to the users. These metrics then are the data transmitted via the radio module, and the raw data is discarded. These algorithms can be as simple as down-sampling schemes to get an estimation of the raw data without the bandwidth requirements, or much more complicated processes. The data can be transmitted to another sensor, to a mobile hub (e.g., cell phone, wrist watch, usb stick, etc.), or to a base station (e.g., computer).

In one embodiment, the present invention includes a muscle sensor system that includes one or more muscle sensor patches, a mobile computing device (e.g., mobile hub) with one or more user interfaces, and a base station. The muscle sensor system can be configured as a multiprocessor biometric transceiver and feedback system. The muscle sensor patches, mobile hub, and base station each are computing devices, with the patches and mobile device having electronic components that operate with a process for data processing. The muscle sensor patches are configured to be worn for a short to long duration by the user, such as during a muscle activity or even over multiple days or a week of muscle activities. The patches are comfortable on the skin due to the lack of adhesive where the conductive gel allows for the sensor elements to float with the skin.

The patches are configured to be disposable. The mobile hub can be configured to common handheld computing devices, and may be configured as a smart phone or the like with advanced wireless communication capabilities so as to be able to communicate data over a mobile communications network or internet. As such, the mobile hub can communicate over a cellular network or link with the internet through Wi-Fi. For example, the mobile hub can be a smart phone having the appropriate software so as to provide the functionalities described herein. In another example, the smart phone can communicate with the sensor patches via Bluetooth communication protocol or similar communication technique. The base station can be any type of personal computer, and any personal computer can be configured into a base station when including the appropriate software. The software of the base station provides the capabilities of base station functionality to any computer, such that the computer can communicate with the mobile computing device and receive, record, and/or process the data obtained by the sensors and transmitted from the mobile computing device. The base station can also provide data or processed muscle data or metrics thereof back to the mobile computing device can provide the processed muscle data or metrics thereof to the user. Visual or audible user interfaces can provide this information to the user, and the user can utilize the information to modulate their performance of a muscle activity.

The configuration of the muscle patch sensors can be integrated sensor-transmitters or sensor transceivers. They may also be referenced as disposable data patches as they may have more capabilities than just measuring muscle data. The mobile computing device can be outfitted with receiver, transmitter, and/or transceiver modules for one way or two way communication links. The mobile computing device can also be outfitted with one or more different types of user interfaces, such as tactile, graphical, or audible. The base station includes hardware and software to implement the functionality as described herein.

In one embodiment, the base station can be operably coupled to a remote computing system, such as a server, that includes a database of muscle data for one or more other users. That is, the data of the database can be provided by multiple users of the muscle sensor systems. The data can be raw or processed for one or more users. The base station can be operably coupled to the remote computing system over a network, such as the internet, or other manner for remote data communications. A base station outfitted with a wireless card for cellular network communications may also be able to communicate with the server to provide or obtain relevant data.

FIG. 1 illustrates various embodiments of the muscle sensor system 100 of the present invention. As shown, a first user 102 includes two different sensor patches 104, 106 adhered to the skin over the back shoulder area and a mobile device 108 worn on the arm. The mobile device also includes an arm strap 110 to allow for wearing on the upper arm. The different sensor patches 104 can communicate wirelessly with the mobile device 108 in order to provide relevant data thereto. The mobile device 108 can communicate with a remote base station 116, which in turn can be operably coupled to a network 118 and through the network 118 to a remote computing device 120, which can be generally referred to as a server 120. The mobile device 108 can also provide data to the user 102, such as visual or audio so that the user 102 can monitor muscle performance as well as overall performance, which can allow the user to adjust the effort or implementation of the muscle activity in order to change the muscle data to a desirable level. The base station 116 may also be operably coupled with a cloud computing 122 system or network.

As shown, a second user 102a includes two different sensor patches 104a, 106a adhered to the skin over the back shoulder area and a mobile device 108a worn on the wrist. The mobile device 108a also includes a wrist strap 110a to allow for wearing on the wrist or forearm. The configuration shown for the second user 102a is substantially the same as shown for the first user 102, with the exception of the mobile device 108 being worn on the wrist similarly to a watch. It should be recognized for user the second 102a or other users that the sensor patches 104a, 106a can be located over any muscle or muscle groups so as to be able to acquire relevant data during implementation of muscle activities.

As shown, a third user 102b includes two different sensor patches 104b, 106b adhered to the skin over the back shoulder area and a mobile device 108b worn in the shoe 112 as well as an audible user interface device 114 worn near the ear. Here, the functionality of the mobile device 108 is divided into a shoe transceiver device 108b and audible user interface device 114. The shoe transceiver device 108b handles data communication between the sensor patches 104b, 106b as well as with the base station 116, while the audible user interface device 114 provides audible information to the third user 102b, such as beeps, words, or combinations thereto. The words can indicate the current muscle data or instructions to improve muscle output based on muscle data.

Figure 2:
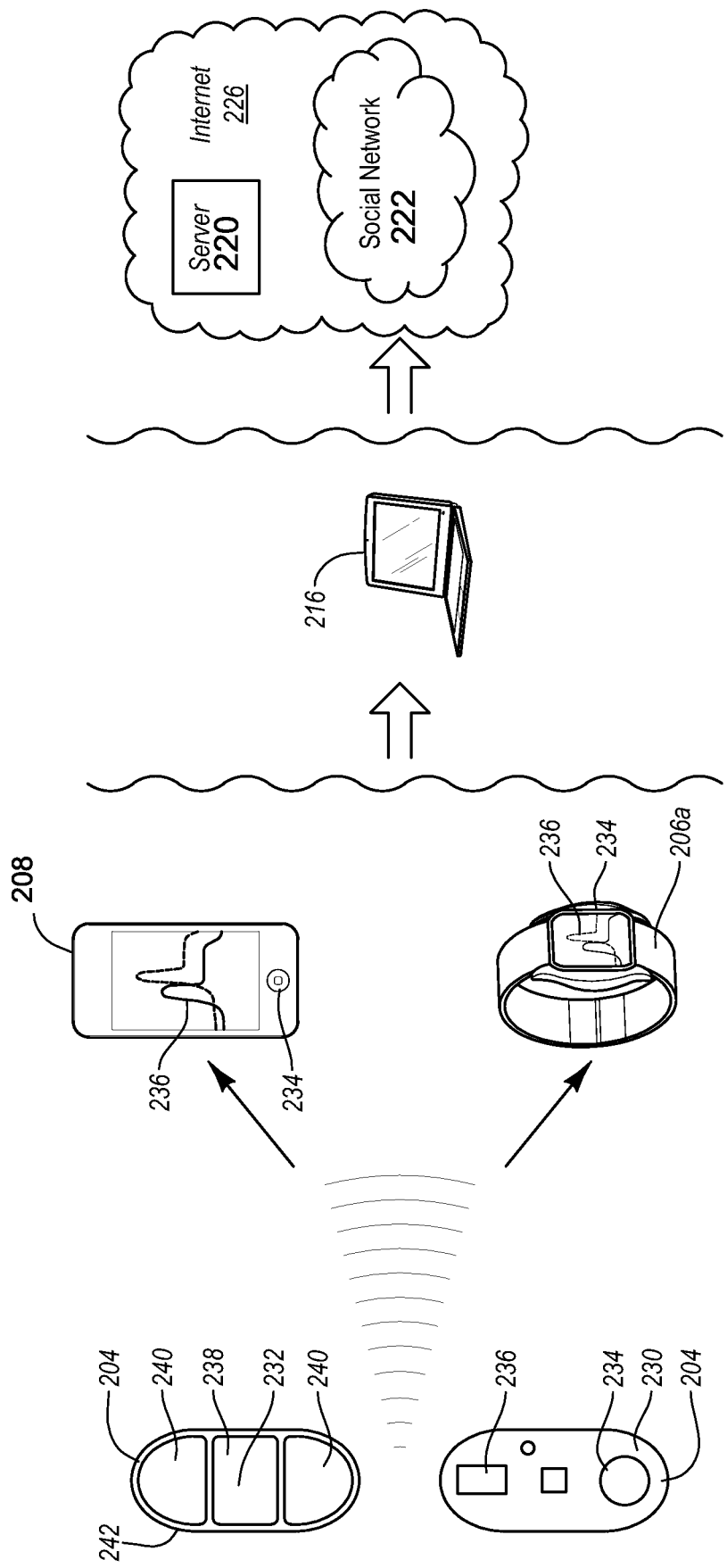
FIG. 2 includes a schematic representation of different embodiments of a base station of a sensor system in communication with a computing system and a social network, where the communication can be over a network.

FIG. 2 includes a schematic representation of different embodiments of sensor system having a sensor patch 204 in communication with a mobile device 208, which can be fastened to a user by a band 206a. The mobile device 208 is in communication with a base station 216 that can be in communication with a network computing system 220, which network computing device can include a social network 222, where the communication can be over a network 226.

The sensor patch 204 is shown with its front side 230 and back side 232. The front side can include user interface controllers 234 and user feedback interfaces 236. The controllers 234 can be any control element found on mobile devices, such as knobs, buttons, keyboard, touchscreen or the like. The feedback interfaces 236 can be visual or audible. When referencing feedback, it is intended that the device provides some feedback of their data so that they can modulate performance. The back side 232 can include a sensor region 238 and one or more adhesive regions 240. Multiple sensor regions 238 may also be included. Also, the back side 232 can include a perimeter or border area 242 that is adhesive, and may be more adhesive than other adhesive regions 240 so as to inhibit edge peel from the skin. Generally, the entire back side 232 can be the skin-adhering surface; however, the specific adhesive regions 240 can be the skin-adhering surfaces while the sensor region 238 can be a non-adhesive region or substantially less adhesive region. It is preferred that the sensor region 238 is not adhesive.

Figure 3A:
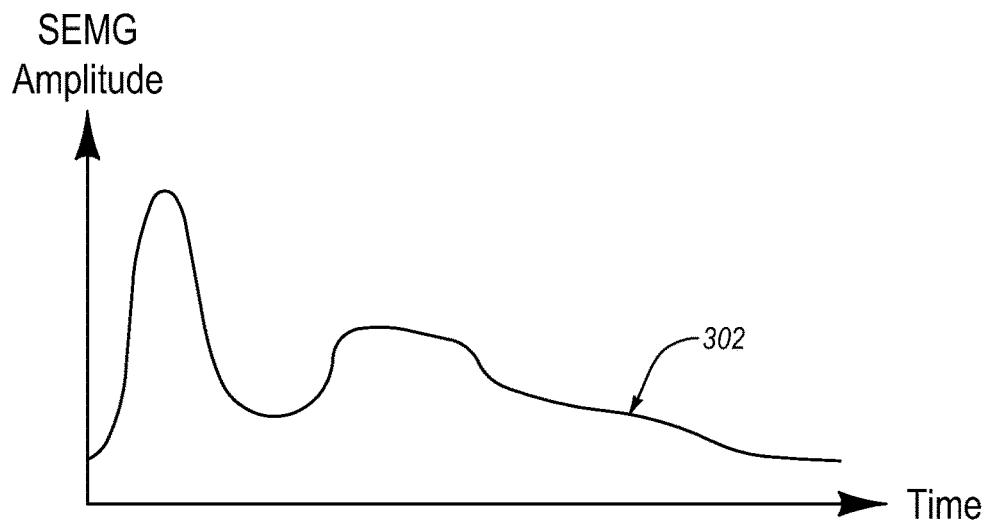
FIG. 3A includes a graph that illustrates sEMG amplitude versus time.
Figure 3B:
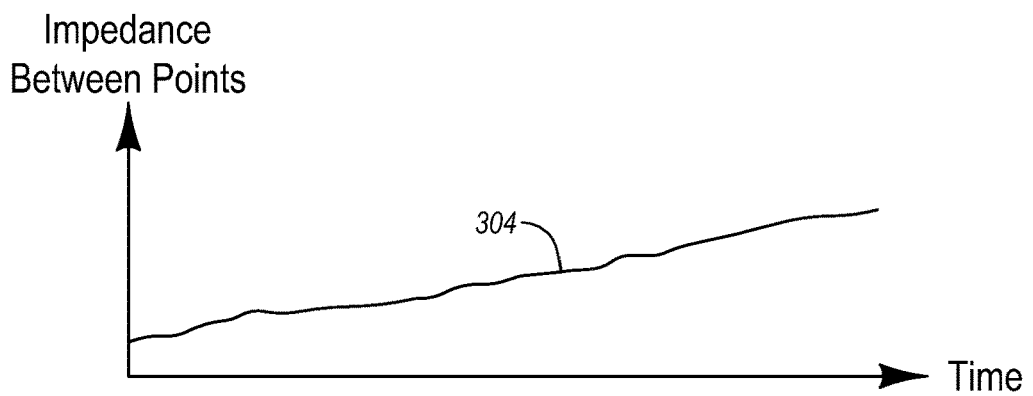
FIG. 3B includes a graph that illustrates impedance between data points versus time.
Figure 3C:
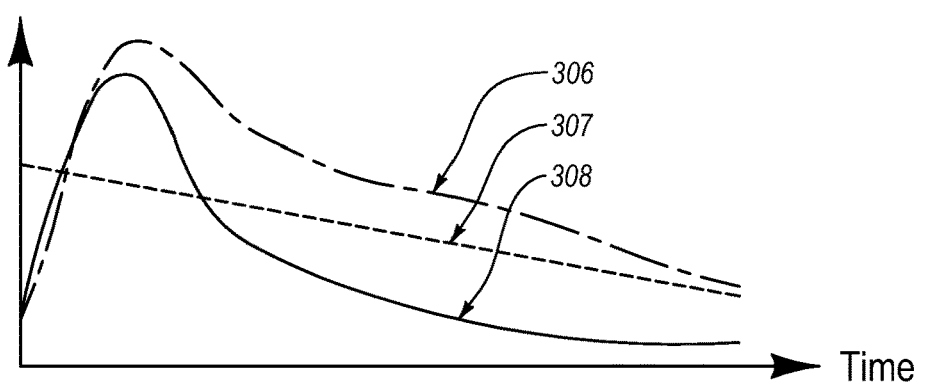
FIG. 3C includes a graph that illustrates: (1) non-impedance adjusted sEMG data versus time; (2); impedance versus time; and (3) impedance adjusted sEMG data versus time.

The feedback interface 236 can be configured for providing graphs of the user's data. FIGS. 3A-3C provide some examples of data graphs that can be provided to a user. FIG. 3A illustrates a graph of sEMG amplitude versus time, which shows a line 302 for sEMG data for a left-upper trapezius, for example. FIG. 3B includes a graph of impedance between data points versus time 304. FIG. 3C shows a comparative analysis of different graphical data, such as: 1) non-impedance adjusted sEMG data versus time 306; (2); impedance versus time 307; and (3) impedance adjusted sEMG data versus time 308. Accordingly, the user can obtain information based on sEMG data, which is the primary measurement modality. Also, additional physiological measurements, such as impedance, can be periodically measured. The impedance can be used to adjust the amplitude of sEMG signals to compensate for impedance changes at the sensor/skin interface due to physiological changes which occur during physiological exertion (see FIG. 3C).

In one embodiment, which the mobile device is a wearable, fully concealable data server with minimal feedback to the user, which allows the user to measure and test physiological response parameters without feedback. As such, the mobile device can be configured as a stealth data server that is hidden from the public and that performs data processing, data storage, and allows for functional physiological testing. The testing can be considered to be blind testing when no feedback is provided to the user. The mobile device can be concealed on the body and in or under clothing.

In one embodiment, a sensor patch can be configured as a reference sensor patch or include a reference sensor thereon. The sensor patch can be configured as an active sensor or include an active sensor thereon. Also, the sensor patch can include one or more active sensors and one or more references sensors. The sensor system can include two different sensor patches, each having one or more active sensors and a reference sensor. The reference sensor can provide a reference measurement point, and may be considered to be a ground with respect to active sensors. The two sensor patch configuration can provide for the two different sensors to be applied to skin apart from each other by some distance. The distance between the two sensor patches can be variable. In some instances, the two patches can be on different muscle groups or adjacent muscle groups. In other instances the two patches can be on the same muscle group. In one aspect, the two sensors can be wired together, and in an alternative aspect the two sensors can communicate wirelessly with each other. As such, both sensors can include transmitters, receivers, and/or transceivers for data communication. When wired, one patch can serve as a data patch and the other patch can be a reference patch, where these two patches can be linked through an insulated conductor line.

Figure 4A:
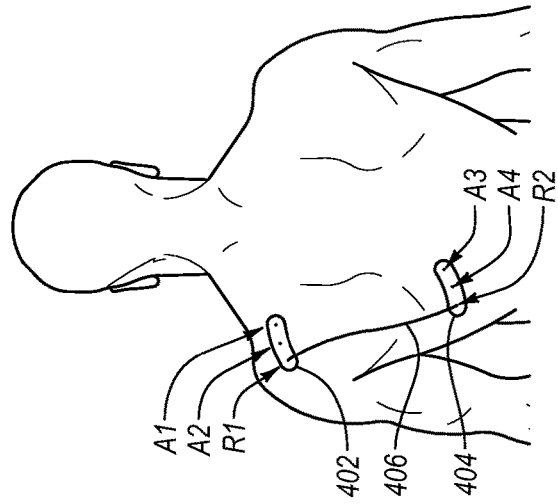
FIG. 4A includes a schematic representation of an embodiment of a sensor system.
Figure 4A:
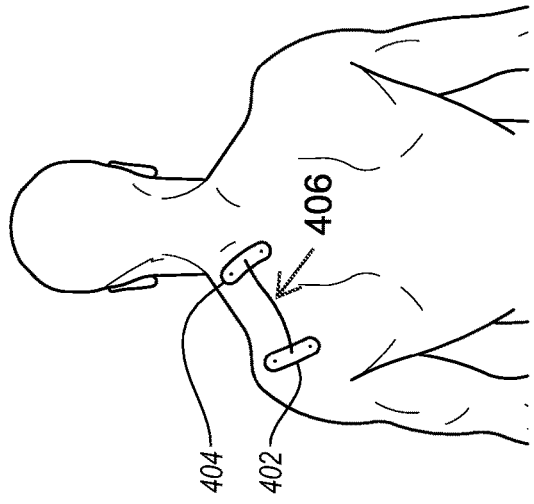
Figure 4A:
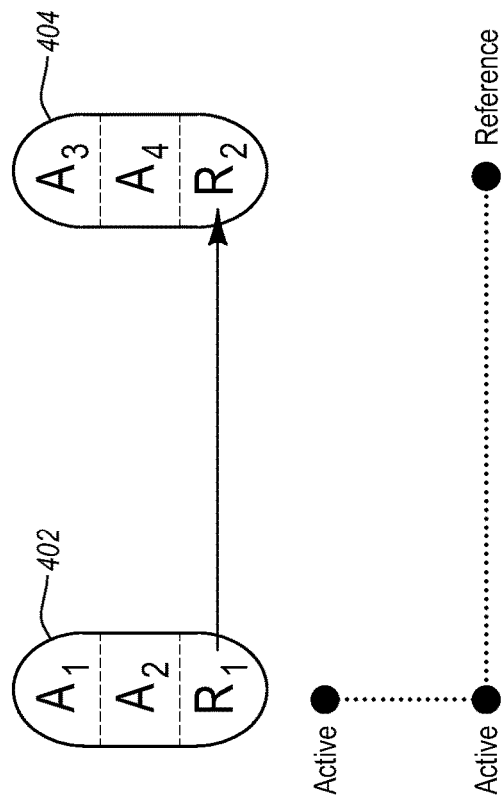

As shown in FIGS. 4A (e.g., showing a first sensor operation mode) and 4B (e.g., showing a second sensor operation mode), the a first sensor patch 402 can include a first active sensor element A1, a second active sensor element A2, and a first reference sensor element R1, and the second sensor patch 404 can include a third active sensor element A3, a fourth active sensor element A4, and a second reference sensor element R2. These different active sensor elements and references sensor elements can operate together to acquire meaningful muscle data.

As shown in FIG. 4A, the first sensor patch 402 can be over the upper shoulder region and the second sensor patch 404 can be on the middle back below the first sensor patch 402 and connected to first sensor patch 402 by connector 406. In this arrangement, the first sensor patch 402 uses both the first active sensor element A1 and second active sensor element A2 to acquire data, which is referenced with the second reference sensor R2 of the second sensor patch 404. FIG. 4A shows that both active sensor elements are on the same patch, and the reference sensor element is remove via a wireless or wired connection.

Figure 4B:
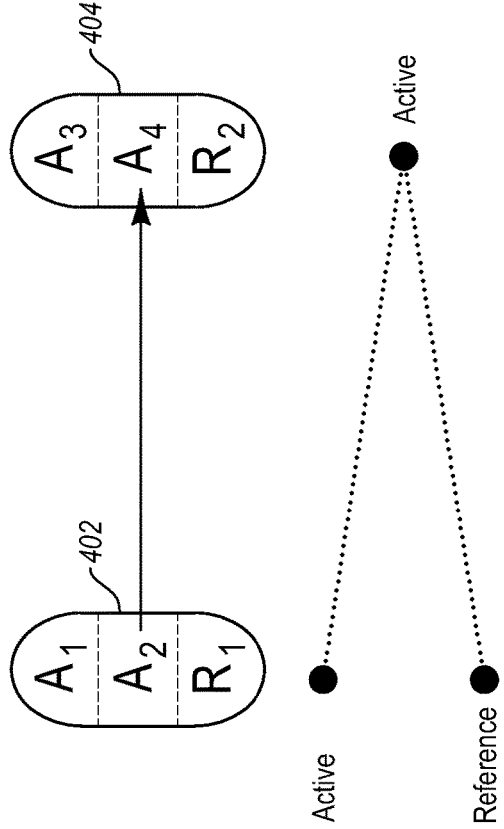
FIG. 4B includes a schematic representation of an embodiment of a sensor system.

As shown in FIG. 4B, the first sensor patch 402 can be over the upper shoulder region and the second sensor patch 404 can be can be located closer to the neck compared to the first sensor patch 402. First and second sensor patches 402 and 404 can also be connected by connector 406. In this arrangement, the first sensor patch 402 uses the first active sensor element A1 and second sensor patch 404 uses the fourth active sensor element A4 to acquire data, which is referenced with the first reference sensor R2 of the first sensor patch 402. While different active sensor and reference sensor operational modes are shown and described, any two active sensor elements and single reference sensor element can cooperate in order to ascertain muscle activity data and reference data. It is shown that in FIG. 4B, the two active sensor elements are remote from each other and on separate patches such that the measurement points for each channel of measurement is non-local. The connection between these active sensor elements on the different patches can be wireless or via an insulated conductor line.

Figure 5:
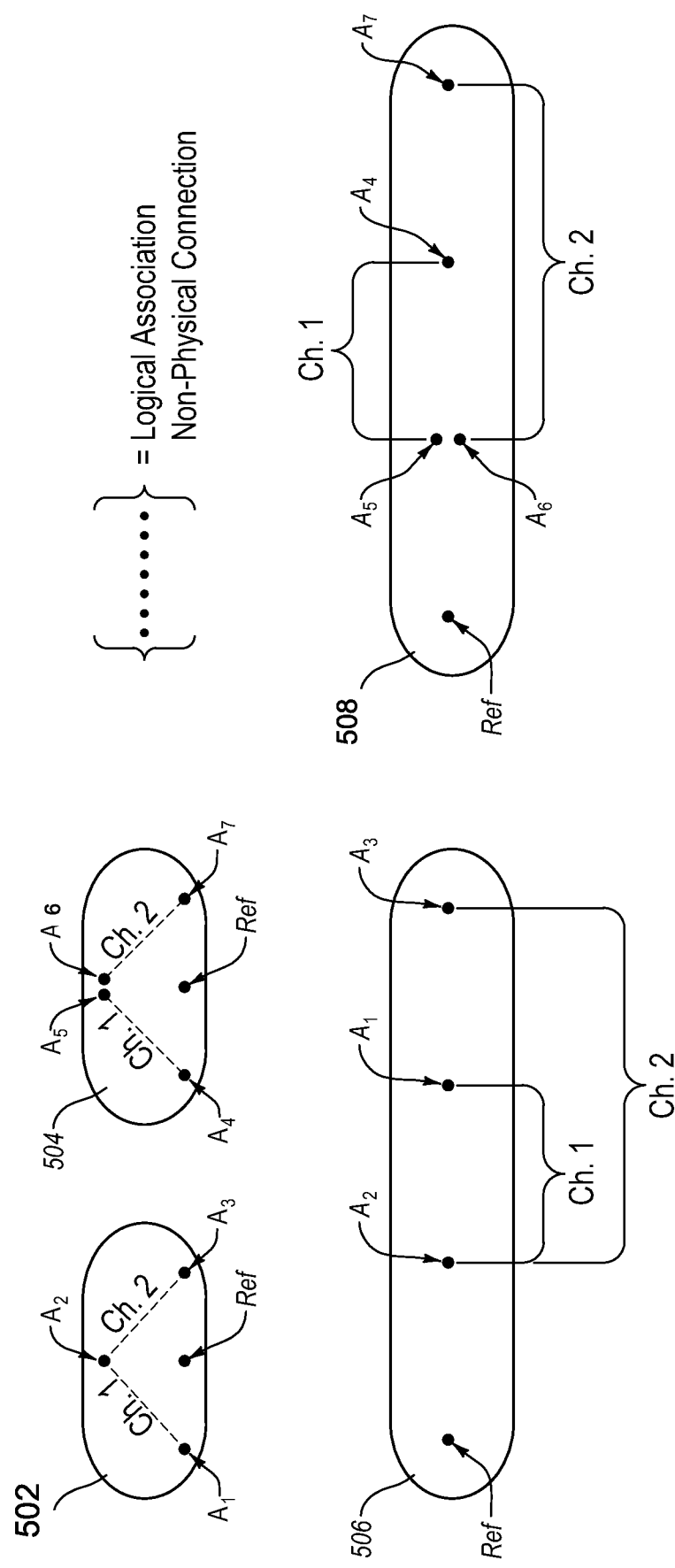
FIG. 5 includes a schematic representation of embodiments of muscle sensors of a sensor system.

FIG. 5 shows alternative embodiments of the sensor element arrangement on the sensor patches. As shown, sensor patch 502 includes a first active sensor element A1 in communication with a second active sensor element A2 over a first channel (e.g., Channel 1). The second active sensor element A2 is in communication with a third active sensor element A3 over a second channel (e.g., Channel 2). The reference sensor (e.g., Ref) is located so as to be between or operably coupled with A1, A2, and A3 active sensors. As shown, sensor patch 504 includes a fourth active sensor element A4 in communication with a fifth active sensor element A5 over a first channel (e.g., Channel 1). A sixth active sensor element A6 is in communication with a seventh active sensor element A7 over a second channel (e.g., Channel 2). The reference sensor (e.g., Ref) is located so as to be between or operably coupled with the A4, A5, A6, and A7 active sensors. As shown, sensor patch 506 includes the sensor elements of patch 502; however, the sensor elements are in a linear arrangement with the reference sensor element being on one end. As shown, sensor patch 508 includes the sensor elements of patch 504; however, the sensor elements are arranged in substantially a linear forma with the reference sensor being at one end. The sensor elements can have substantially any arrangement on a sensor patch. The channels can be wireless with no physical connection, such that there is a logical association therebetween. Thus, the each patch can include more than one data input channel, which may include at least two different inter-electrode spacing configurations on a single patch.

Figure 6A:
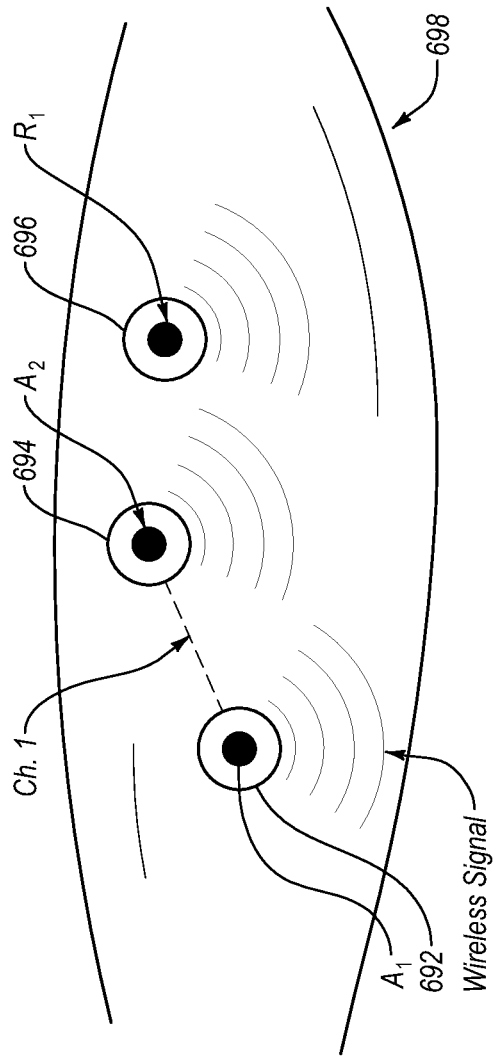
FIG. 6A includes a schematic representation of an embodiment of muscle sensors of a sensor system, where all sensor elements are isolated.

FIG. 6A shows an embodiment of sensor patches that include only a single sensor element. As shown, a first sensor patch 692 has a first active sensor element A1, which first sensor patch 692 is operably coupled a second sensor patch 694 having a second active sensor element A2, wherein the operable coupling is wireless such that the channel (e.g., Channel 1) has no physical connection. Also shown is a reference sensor patch 696 having a reference sensor element R1. Each of the first active sensor element A1, second active sensor element A2 and reference element R1 can be in wireless communication with the mobile device, which can receive the data and transmit the data to the base station. The sensors are shown to be adhered to skin over a muscle 698.

Figure 6B:
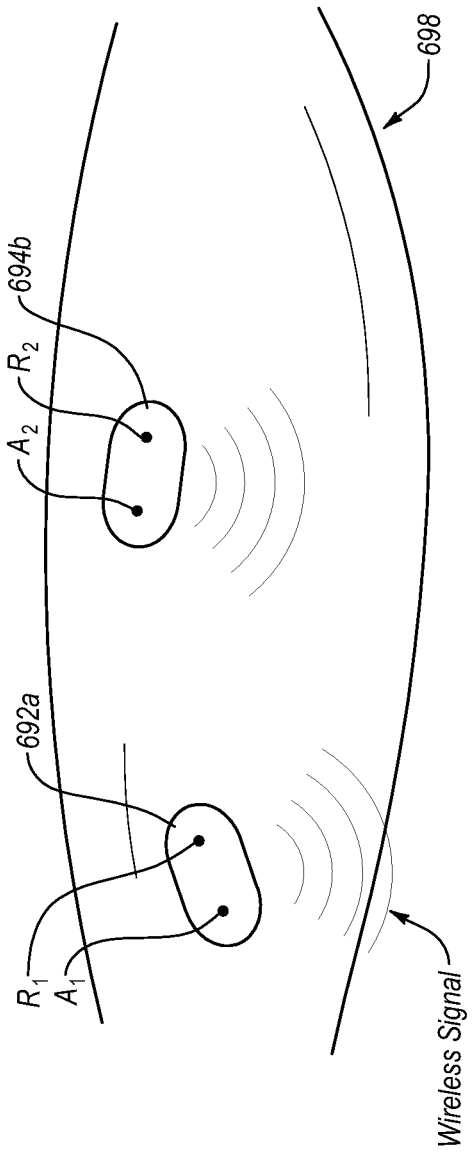
FIG. 6B includes a schematic representation of an embodiment of muscle sensors of a sensor system, where some of the sensor elements are grouped.

FIG. 6B shows an embodiment of sensor patches that include two sensor elements, and each sensor patch includes an active sensor element and a reference sensor element. As shown, a first sensor patch 692a has a first active sensor element A1 and a first reference sensor element R1 that are operably coupled while being on the same patch 692a. The second sensor patch 694b is shown to have a second active sensor element A2 and a second reference sensor element R2. Each of the first active sensor element A1, second active sensor element A2, first reference sensor element R1, and second reference sensor element R2 can be in wireless communication with the mobile device, which can receive the data and transmit the data to the base station. The first patch 692a can have each sensor element sending wireless data, or one transmitter element that sends data for the A1 and R2 sensors. The second patch 694b can be similarly configured for communication with the mobile device. The sensors are shown to be adhered to skin over a muscle 698.

In accordance with FIGS. 6A-6B, the present invention may be configured to operate without measuring data with bipolar instrumentation and/or operational amplifiers. Instead, the present invention can be configured for monopolar data input.

The sensor system may include additional firmware or software filters to eliminate common-mode signals. Common-mode rejection is usually handled by bipolar instrumentation amplifiers, by the nature of their design.

FIG. 7A includes a schematic representation of components useful for processing physiological data, such as sEMG and/or ECG, which can be included in the sensor patch or the mobile device. It can be beneficial to include these components on the sensor patch to improve functionality thereof. However, there may be instances where these components are included on the mobile device. In any event the raw data obtained by the sensor is processed. The processed data can then be sent wirelessly from the sensor patches to the mobile device, or from the mobile device to the base station.

Further the data can be sent to the remote computing system or server over a network. FIG. 7B shows an alternative microcontroller that includes the ADC component as well as wireless transmitter component. The microcontroller can be configured for EMG and/or ECG data.

As shown, the data processing components can be sEMG data components 700 that include a specialized configuration of filters and amplification levels optimized for surface electromyography (sEMG). These filters and amplification level settings may be achieved by including: high pass filter 702, low-pass filter 704, band-pass filter (not shown), one or more notch filter(s) 706, a RMS calculation (Root Mean Square) unit 708, and/or a data smoothing unit 710. The data smoothing unit can be a floating average, or trailing average, for example, in which the average of the last "n" samples is used to replace the current displayed data point. This configuration can provide data output to the microcontroller 726 or to the mobile device for amplification (e.g., amplifier 722) and analog to data conversion (e.g., ADC 724).

Also shown, the data processing components can be ECG data components 721 that include a specialized configuration of filters and amplification levels optimized for ECG. These filters and amplification level settings may be achieved by including: high pass filter 712, low-pass filter 714, band-pass filter (not shown), one or more notch filter(s) 716, a RMS calculation (Root Mean Square) unit 718, and/or a data smoothing unit 720. This configuration can provide data output to the microcontroller 726 or to the mobile device for amplification (e.g., amplifier 722) and analog to data conversion (e.g., ADC 724).

The output data can input EMG and/or ECG, which is input to the microcontroller 726. Before reaching the microcontroller 726, the data can be amplified with the amplifier 722 and converted to digital data by the ADC 724. The microcontroller 726 can include firmware as necessary for the implementations. When both EMG and ECG data is obtained, the microcontroller 726 can use an EMG module 728, such as in Mode 1, or an ECG module 730, such as in Mode 2. The microcontroller 726 can switch between Mode 1 and Mode 2. The microcontroller 726 can include firmware specially designed to be able to easily switch between specialized sEMG configuration and specialized ECG configuration.

The data from the microcontroller 726 can then be transmitted by a transmission module 732. When the microcontroller 726 is on the sensor patch, the transmission module 732 can be a transmitter. When the microcontroller 726 is on the mobile device, the transmission module 732 can be a transceiver module with a transmitter and receiver.

As shown in FIG. 7B, the amplifier 722 can be a separate module; however, the ADC module and transmitter module can be integrated into the microcontroller 734. In one example, the transmitter can be a bluetooth-type transmitter when on the sensor patch. Preferably, the components of FIGS. 7A and 7B are located on the sensor patch, and the transmitter transmits the processed data to the mobile device.

Figure 8A:
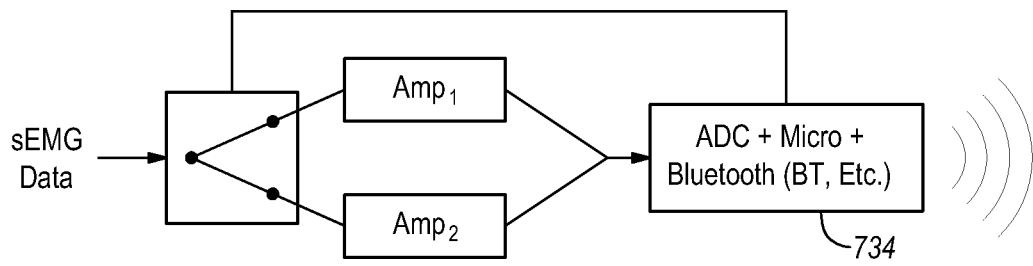
FIG. 8A includes a schematic representation of variable-gain amplification modules of a microcontroller of a base station of a sensor system.

FIG. 8A shows an embodiment that includes a variable-gain amplification configuration that is controlled by the microcontroller 734. This variable-gain amplification configuration can include a first amplifier Amp1 and a second amplifier Amp2, which are controlled by the controller 734. As such, the controller 734 an control whether the data is processed with the first amplifier Amp1 and/or the second amplifier Amp2. This can include soft switch controls that have access to two or more amplification levels, which are also controlled by the microcontroller 734.

Figure 8B:
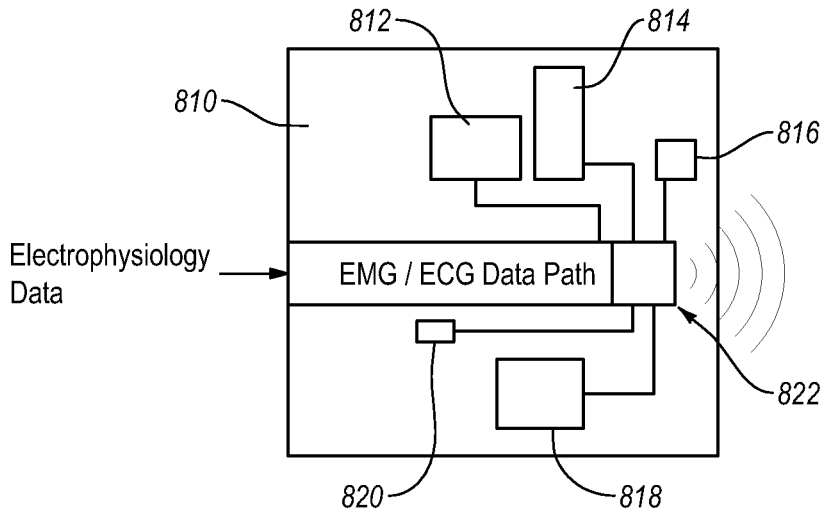
FIG. 8B includes a schematic representation of a base station that includes an ECG module, accelerometer module, GPS module, temperature module, impedance module, GSR module, and an EEG module.

FIG. 8B illustrates an embodiment of sensor patch 810 having additional data modules. The additional data modules can include an ECG module (not shown), accelerometer 812, a GPS module 814, a temperature module 816, an impedance module 818, a GSR module 820, and/or an EEG module. All of these modules can be under the control of the microcontroller 822. Advances in engineering now allow for all of these modules to fit on a flexible sensor patch.

Figure 8C:
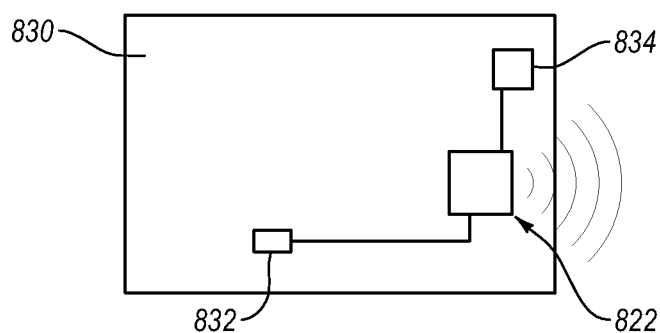
FIG. 8C includes a schematic representation of a base station that includes only a single module, such as sEMG, ECG, accelerometer, GPS module, temperature module, impedance module, GSR module, and an EEG module FIG. 9A includes a schematic representation of a subject outfitted with an embodiment of a sensor system.

FIG. 8C illustrates a sensor patch 830 that includes only one sensor module 832, a power module 834 (e.g., power module can be on all of the sensor patches described herein), and the microcontroller 822. The configuration of the sensor module 832 can be selected from the group consisting of sEMG, ECG, accelerometer, GPS, temperature, impedance, GSR, or EEG modules.

While many of the embodiments described herein can include the sensor patches being located on skin areas relatively close together, the different sensor patches may also be distant from each other. This can include one sensor patch being on limb, and the other sensor patch being on the other limb. Optionally, the sensor patches can be on corresponding muscle groups, such as right and left muscle groups.

Figure 9B:
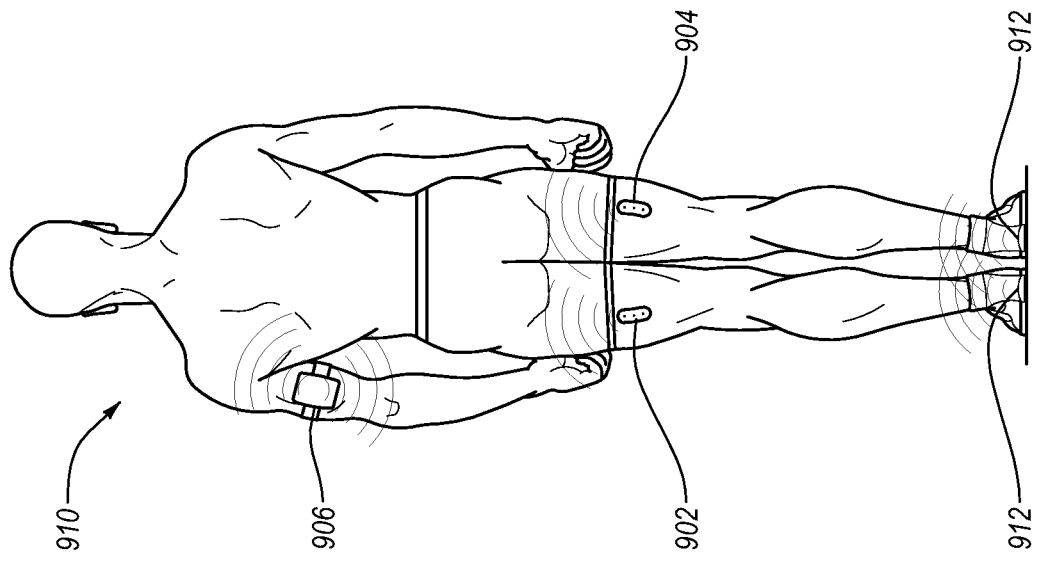
FIG. 9B includes a schematic representation of a subject outfitted with another embodiment of a sensor system.
Figure 9A:
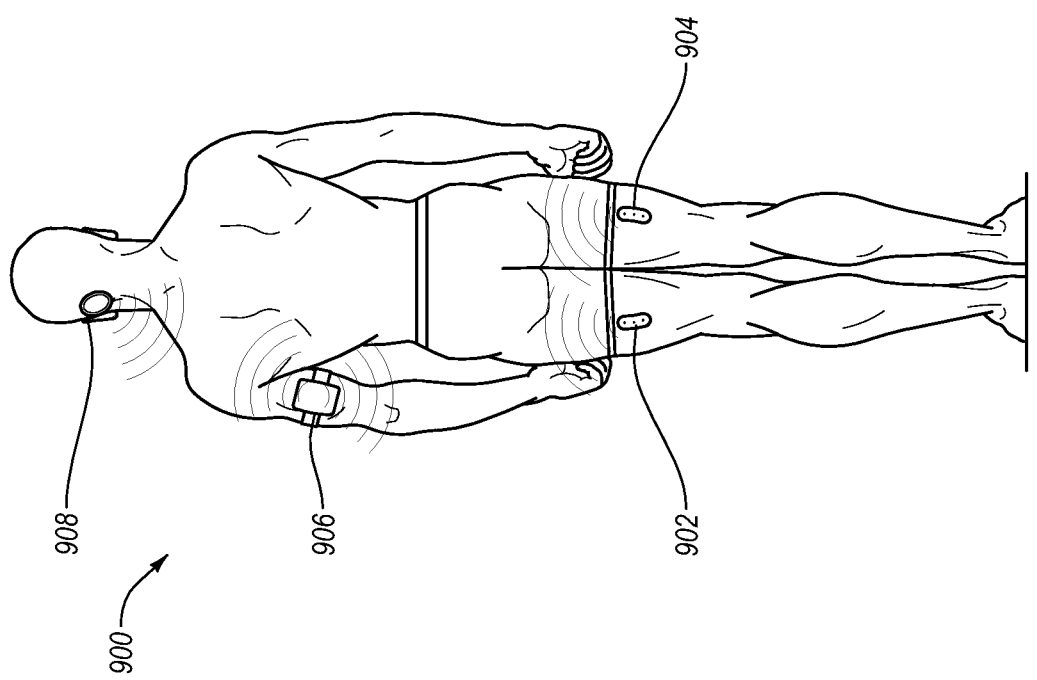

FIG. 9A illustrates one embodiment of a sensor system 900 arrangement that includes a first sensor patch 902 on a first limb and a second sensor patch 904 on a second limb. The sensor patches 902, 904 may or may not be on corresponding muscle groups.

The sensor patches 902, 904 are in communication with the mobile device 906, which in this embodiment is configured for wearing on the upper arm. Here, the user may not be able to get good visual feedback from the mobile device 906, and as such the system 900 further includes an audible feedback device 908. The audible feedback device 908 can provide sound and word cues to the user regarding their performance, and may even provide instruction on how to improve performance. The audible feedback device 908 can provide feedback via an adhesive patch which is applied behind the ear (not in it) and which transmits sound via the skull to the ear. Other audible device configurations can be used.

FIG. 9B illustrates one embodiment of a sensor system 910 arrangement that includes a first sensor patch 902 on a first limb and a second sensor patch 904 on a second limb. The sensor patches 902, 904 may or may not be on corresponding muscle groups. The sensor patches 902, 904 are in communication with the mobile device 906, which in this embodiment is configured for wearing on the upper arm. This system 910 also includes a pressure sensor 912 for each foot. The pressure sensors 912 can be configured similarly to the sensor patches described herein and can include a pressure sensing element. The pressure sensors 912 can obtain pressure data for each foot as the foot strikes the ground, which can be suitable for jogging and running The pressure sensor 912 can provide the pressure data to the mobile device 906, which in turn can provide suitable information to the user about the force of their heel strikes as well as their gait, and thereby the user can modulate how they are jogging or running The system 910 can include one or more wireless pressure sensor 912, which may be worn under the feet of the user, or integrated within the user's shoes. The pressure sensors can provide feedback to the user, such as the force generated during the heel strike or information about their gait.

The sensor patches can be configured with one or more sensor elements as described herein. As such, the skin-contacting surface of the sensor patches can be designed to improve wearability by each area of the skin-contacting surface being associated with a conductive member that contacts the skin. The conductive member can be electrically conductive and gelatinous or have some form of shape memory. The conductive member can be similar to the ultrasound gel that is commonly used; however, the gel can be rigid or semi-rigid to make an integral device. The conductive member can be adhesive, low adhesive, or non-adhesive.

Figure 10A:
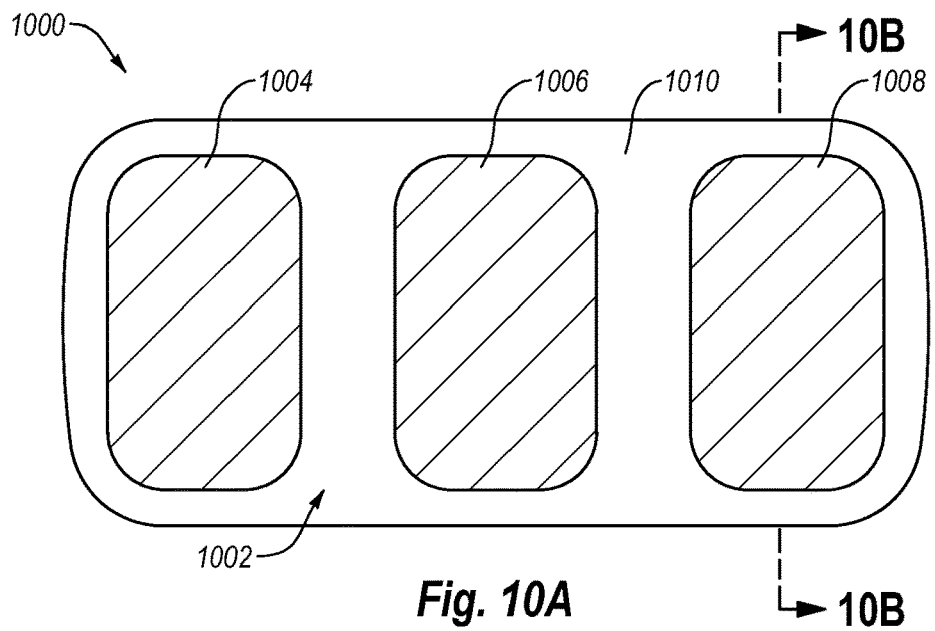
FIGS. 10A-10B include schematic representations of a bottom view (FIG. 10A) and a side view (FIG. 10B) of a muscle sensor patch of a sensor system.
Figure 10B:
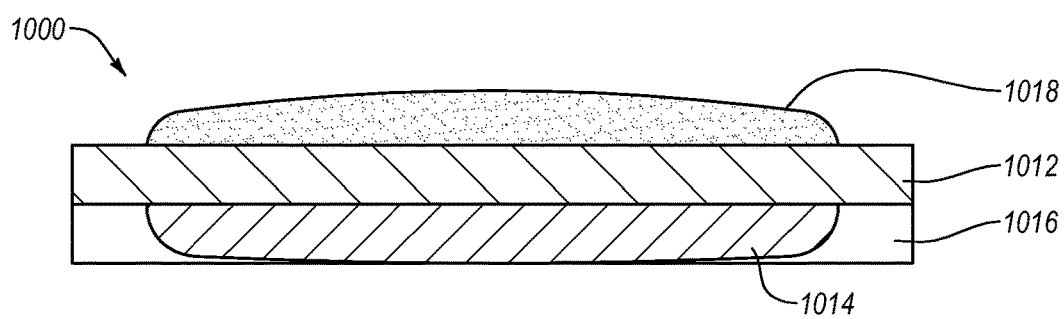
Figure 10C:
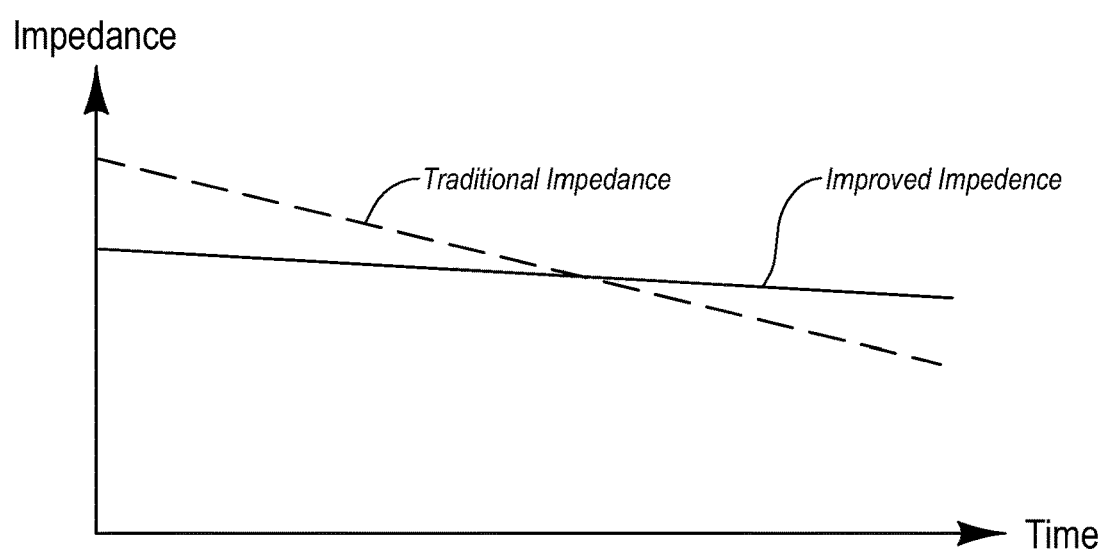
FIG. 10C includes a graph that illustrates impedance versus time.

FIG. 10A illustrates an embodiment of a sensor patch 1000 that has a skin-contacting surface 1002 that is partitioned into three sensor zones, a first active sensor zone 1004, a second active sensor zone 1006, and a reference sensor zone 1008. The border 1010 surrounding these sensor zones is adhesive or highly adhesive. FIG. 10B illustrates a side view of this sensor patch 1000, and shows a module substrate 1012 that includes the modules as described herein. The side view also shows the sensor zones 1014 and adhesive zones 1016, opposite of the flexible pouch 1018 that can be included to contain and protect the components from body secretions or other contaminants. This configuration can improve impedance. FIG. 10C shows traditional impedance (sloped) and the improved impedance that is substantially constant and significantly less sloped.

The sensor patches can be prepared in two different designs for the skin-contacting surfaces. In the first design, two types of material are utilized, both of which are equally adhesive. One material is adhesive and conductive, and the other is an adhesive insulator. They can be of equal height, and with no visible boundary between one and the other. In this manner, the entire surface adheres equally well. The significant difference between these sensors and sensors manufactured today is that in dynamic exercise, high adhesion is critical to long-term, intensive physical activity. The decrease in adhesion in the conductive areas of traditional sensors has produced loss of contact, increased impedance, and loss of signal quality over long testing times (t>20 minutes). It is possible to create a different sensor configuration that facilitates the removal of sweat and oil from the surface of the skin by arranged layers on sensor material that have different hydrophobic properties.

Figure 11A:
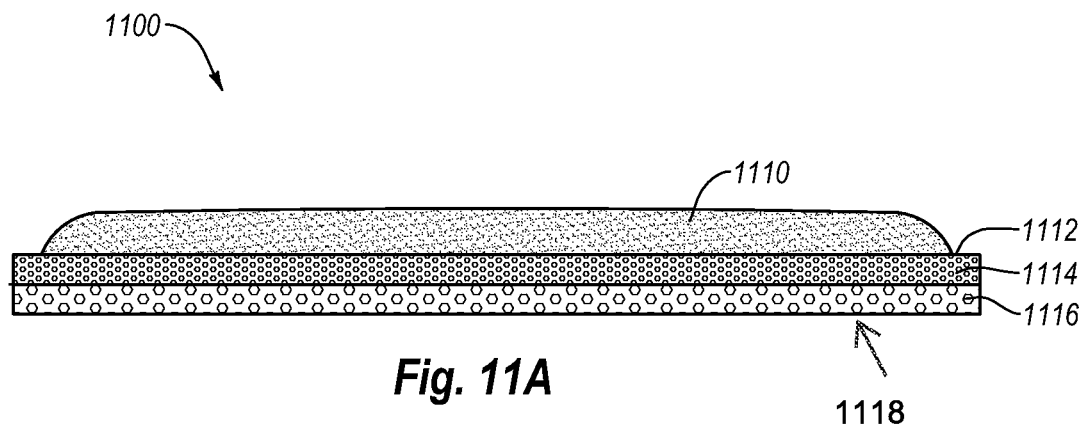
FIGS. 11A-11C include schematic representations of embodiments of a muscle sensor patch of a sensor system.
Figure 11B:
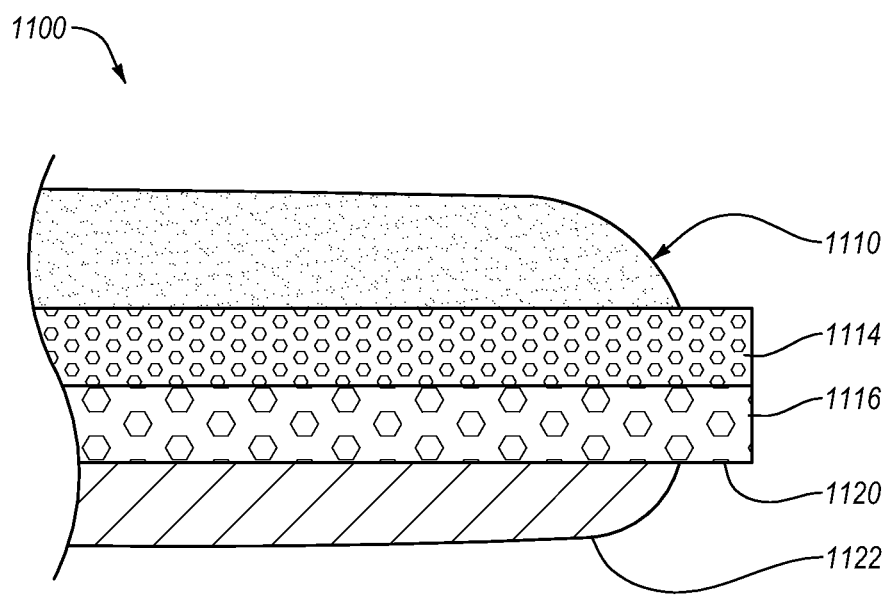

FIG. 11A illustrates an embodiment of the sensor patch 1100 that includes a module pouch 1110 a flexible module substrate 1112, a porous absorbing substrate 1114, and a porous adhesive substrate 1116. The electronic components of the modules can be protected in the module pouch 1110, where the modules can be encased in a gas, liquid, gel, or solid environment. Inert gases or non-conductive liquids can be used to protect the electronics and provide flexibility along with the flexible material of the module pouch 1110. Solid encasings, such as elastomer polymeric or rubber-like encasings can also be uses to form the module pouch 1110. The porous absorbing substrate 1114 can absorb body fluid along with any other liquids from porous adhesive substrate 1116, which wicks the body fluid away from the skin-contacting surface 1118. This allows the porous absorbing substrate 1114 to function as a sponge or reservoir for body fluids and other liquids in order to keep the skin-contacting surface 1118 as dry as possible. The wicking function of the porous adhesive substrate 1116 is preferred to be as high as possible.

In one example, the porous absorbing substrate 1114 can be a hydrophilic layer, and the porous adhesive substrate 1116 can be a hydrophobic layer. The hydrobobicity/hydrophilicity can be relative to each other or standards. The porous absorbing substrate 1114 can have a higher pore volume for greater water retention. The porous adhesive layer 1116 can have pores configured to promote wicking by capillary action.

The skin-contacting surface 1118 can include a porous adhesive conduction area 1120 surrounded by a border of a porous adhesive non-conduction area 1122. The In the second design, the overall layout is similar to the sensor patch 1100 described above for the first design. However, there are multiple layers of the above pattern of materials and portioning of materials for being used for conductors and insulators. When a user has completed a finite number of uses of the sensor (such as a single use) they would remove the top layer. Since the conductive and non-conductive areas are cast together with the same exact height, and no boundary distinctions visible, the entire surface of the electrode can be peeled off and discarded, revealing a fresh layer that is free of oils, hair, dirt, and/or other residue which may remain from the skin after a lengthy workout. In this manner, a single sensor may be reused a number of times, depending on the number of layers present.

Figure 11C:
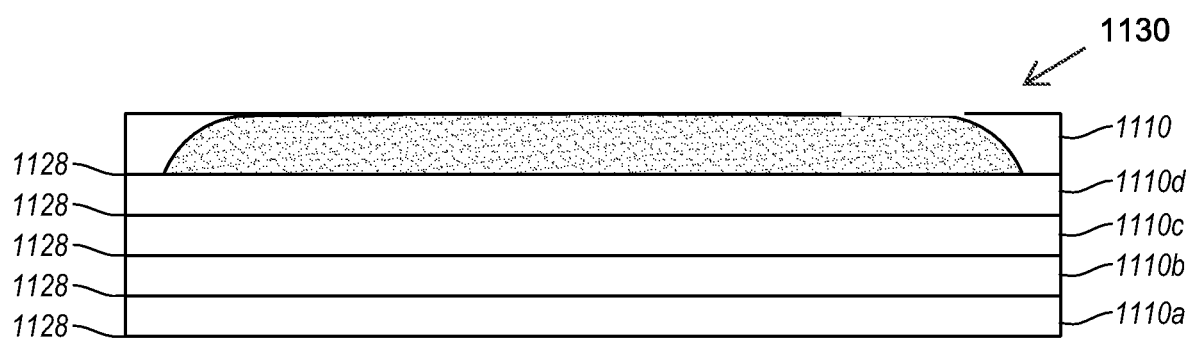

The sensor patches of this second design include sensor modules that can be used repeatedly. The skin-contacting surface is usually the surface that becomes less effective over time and repeated uses. As such, the skin-contacting surface can be integrated, laminated or otherwise configured with the integrated substrate having both of a wicking layer (e.g., also adhesive or having adhesive thereon) and an absorption layer so as to be peelable. FIG. 11C shows such a configuration with a layered sensor patch configuration 1130 that includes a first skin-adhering integrated substrate 1110*a*, a second skin-adhering integrated substrate 1110*b*, a third skin-adhering integrated substrate 1110*c*, and a fourth skin-adhering integrated substrate 1110*d*. It may be possible to have any desired number of skin-adhering integrated substrates depending on thickness factors.

Figure 13:
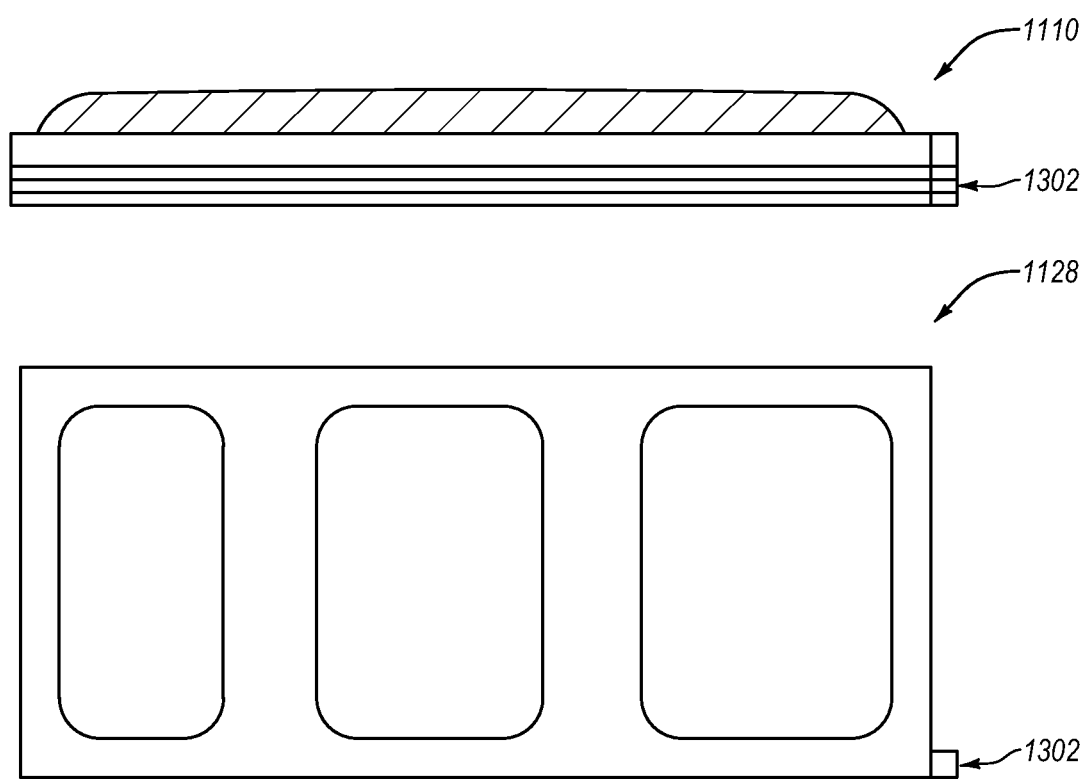
FIG. 13 includes a schematic representation of a sensor patch having a peel tab.

In one embodiment, a peel liner 1128 can be used between each integrated substrate to promote peeling. FIG. 13 illustrates the peel liner 1128 having a tab 1302 that facilitates the peeling action. The peel liner 1128 can have the same conductive area and nonconductive areas as the other layers so that the sensor modules work. Alternatively, the skin-contacting substrate can include the tab 1302.

Figure 11D:
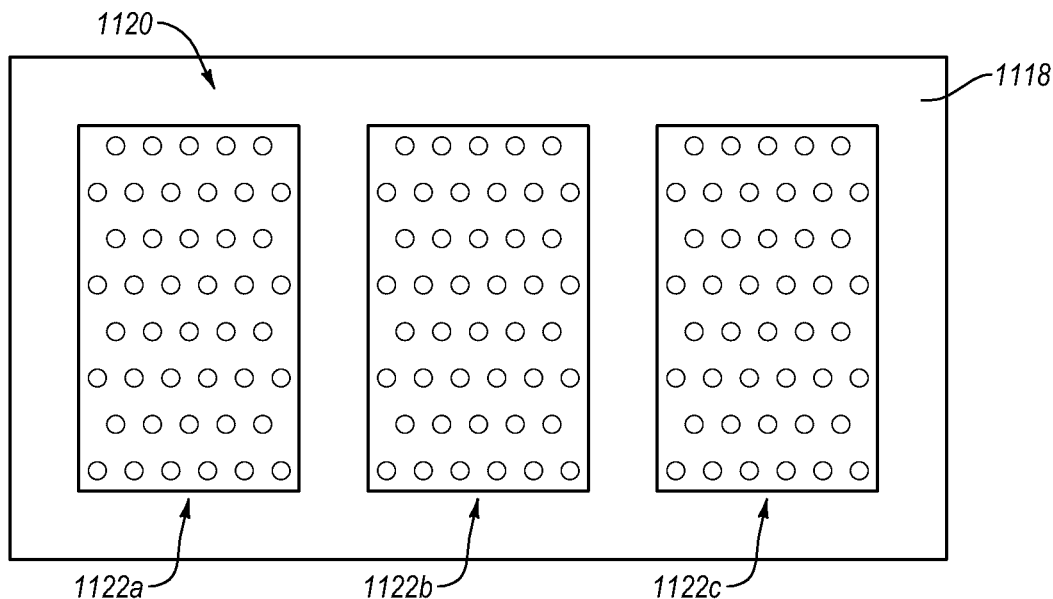
FIGS. 11D-11E include schematic representations of embodiments of skin-adhering surfaces of the muscle sensor patches of FIGS. 11A-11C.
Figure 11E:
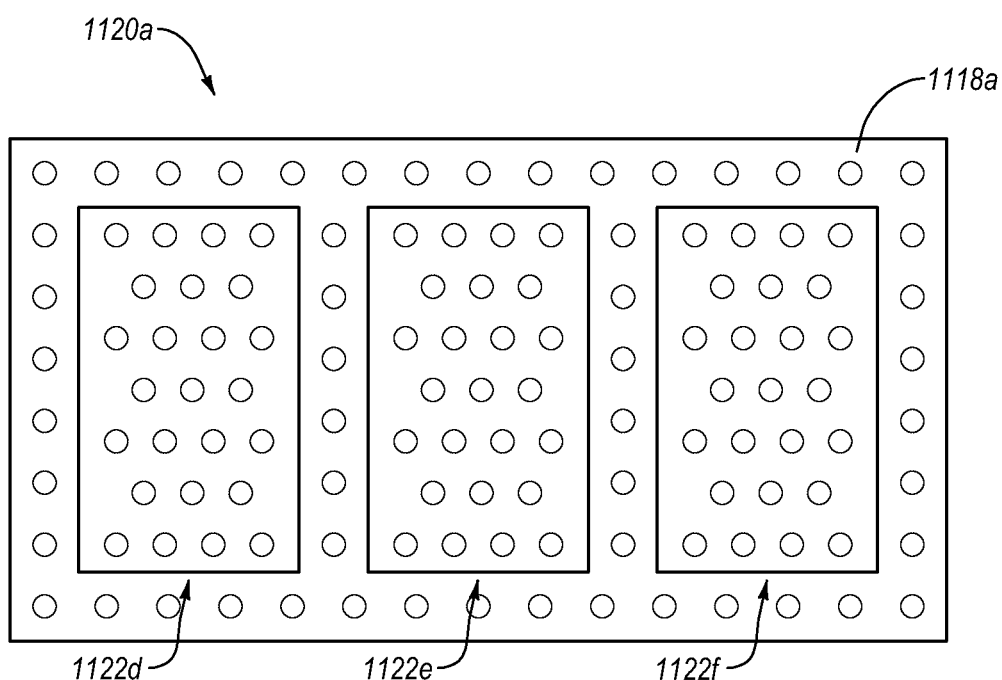

FIG. 11D shows an embodiment of the skin-contacting surface 1118 partitioned into a border region 1120 and a conductive region 1122*a*, 1122*b*, and 1122*c*. The border region 1120 can include a material that is non-porous, non-conductive and hydrophobic so as to provide an insulating function. This border region 1120 can include a layer of adhesive, such as pressure sensitive adhesive. The conductive regions 1122*a*, 1122*b*, and 1122*c* can include a material that is porous, conductive, and hydrophobic, and it may also optionally have an adhesive layer. It can be preferred that the border region 1120 adhesive have higher adhesion with skin. FIG. 11E shows the skin contacting surface 1118*a* partitioned into a porous, adhesive, non-conducting, and hydrophobic border 1120*a*, and a porous, adhesive, conducting, and hydrophobic layer and a conductive region 1122*d*, 1122*e*, and 1122*f*. Accordingly, both a conducing region and non-conducting region can be a useful configuration for the skin-contacting surface 1118*a*.

In one embodiment of the multi-sensor layered configuration, the decrease in layer count affects the impedance between the muscle signal and the device which is acquiring the signal. If the device measures impedance, it can compensate for changes in impedance due to layer removal, and compensate by adjusting the amplification of the signal that is detected. The direct change in the signal can be measured and built into the signal, and adjusted according to the number of layers that have been used. The adjustment can be manual or automatic by the sensor patch. When manual, a button sensor patch associated with the modules can be used to provide an indication that a calibration needs to be performed due to layer removal. The entire sensor patch can be worn for some time, and then peeled from the skin in order to perform a calibration. At this time, it would be suitable to remove the skin-contacting substrate layer.

Figure 14:
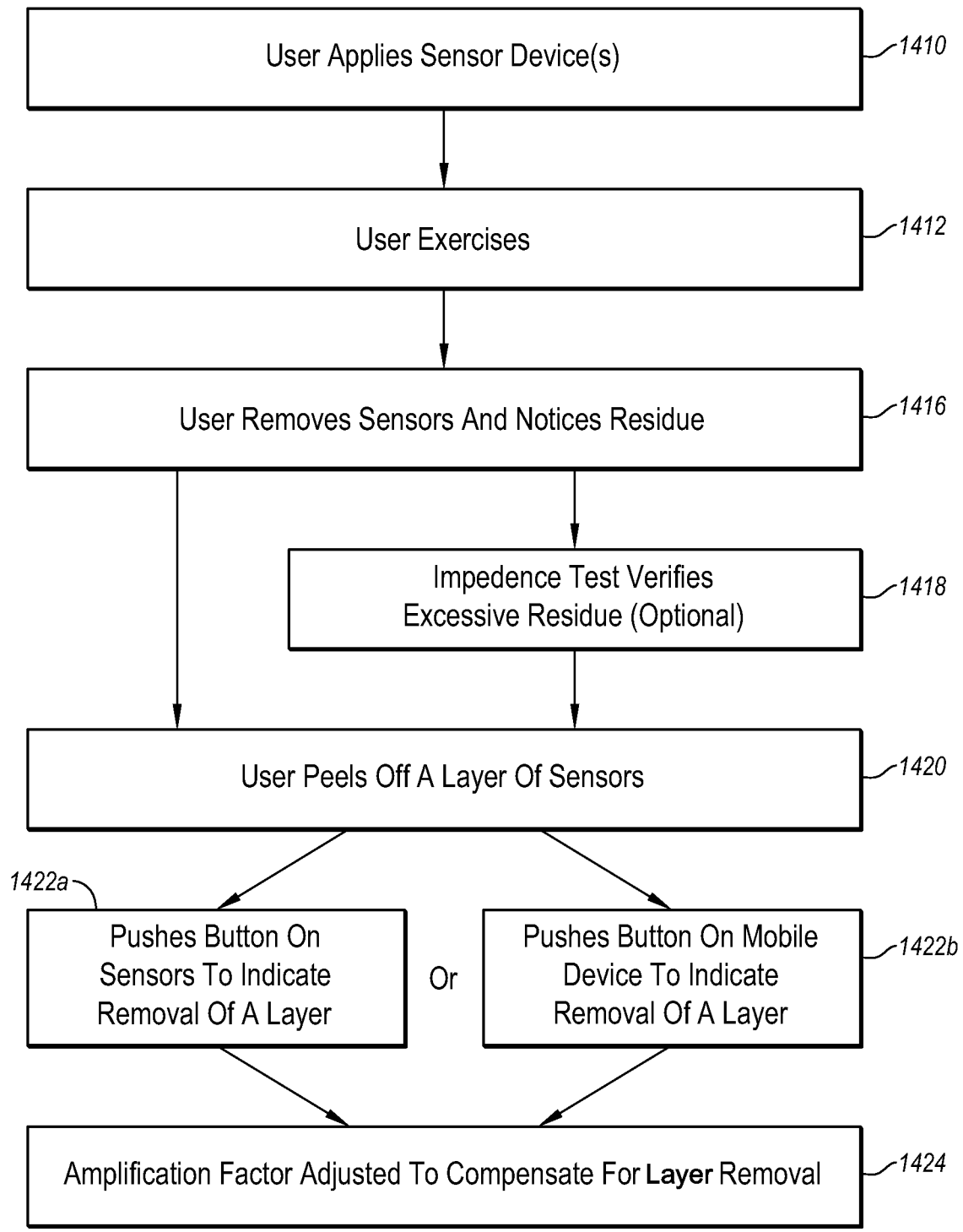
FIG. 14 includes a flow diagram of an embodiment of using a sensor system.

FIG. 14 illustrates a method of using a sensor patch that includes multiple skin-contacting substrates that can be peel to reveal a fresh skin-contacting surface. The method can include a user applying one or more of the sensor patch devices to their skin, and operably engages it with the mobile device (block 1410). The user then exercises with the sensor patches (block 1412). The user then removes the one or more sensors from the skin, and notices a residue on the skin contacting surface (block 1416). Optionally, the user performs an impedance test to verify whether or not the residue is affecting proper function (block 1418). The user peels off a peelable skin-contacting layer from the sensor patch (block 1420). In one option, the user pushes a button on the top of the sensor patch to indicate removal of a peelable skin-contacting layer (block 1422*a*). In another option, the user pushes a button on the mobile device to indicate removal of the peelable skin-contacting layer (block 1422*b*). The amplification factor is adjusted to compensate for removed layer (block 1424).

The inventive skin patches are configured such that the non-adhesive central area has an electronics module mechanically and electrically coupled to the flex sensor on the side opposite of the skin-contacting surface. This connection of the detachable electronics module over a non-adhesive region allows for re-introduction of flexibility and/or damping in all 3 axes of movement. The flex adhesive sensor patch can be shaped or molded to increase strain relief and flexibility in all 3 axes, and pieces of material can be selectively removed to increase flexibility as well.

The current invention includes a paradigm shift in the mechanical understanding of adhesive poly-input patch devices that must function to measure data while adhesively attached to the skin. The sensor patches are configured to provide skin-stretch flexibility and impact damping for two-piece biometric sensor/transceivers in all 3 axes. This can reduce pre-amplified noise from motion artifact.

In one embodiment, the sensor patch can have the electronics module detachably coupled to the part of the flex sensor piece that adheres to the skin. The electronics module can couple with a portion that includes the conductive materials. Optionally, the electronics module can couple with a portion that is conductive and non-adhesive, or which has adhesive which is masked by a thin flexible film of non-adhesive material.

In one embodiment, the sensor modules are configured to provide a sensor patch that is wireless, has dual-element modules, is partially flexible, and is partially non-adhesive. The sensor patch is configured to be capable of biopotential measurement and/or processing and/or transmission by including the proper modules.

In one embodiment, the sensor patch is configured to be partially flexible, partially inflexible, partially adhesive and partially non-adhesive, and include a disposable sensor element that is detachably coupled to a module containment element (e.g., either inflexible or flexible) that includes and encloses all of the electronics components (e.g., including hardware, firmware, and or software configured for amplification, signal filtration, ADC, microcontroller processing, and wireless transmission via a wireless protocol. The detachable coupling advantageously occurs in a non-adhesive area. On one option, there are two or more non-adhesive regions and one or more adhesive regions that surround the non-adhesive regions. The non-adhesive regions can be conductive, while the adhesive regions can be non-conductive. Any reasonable number of conductive and non-conductive regions can occur depending on the sensor modules. The more different types of sensors, the more isolated conductive areas.

In one embodiment, the flexible sensor element and electronics module are electrically and mechanically coupled by: direct connection by means of mechanical interlock force; resilient conductor connections (e.g., for example pin connections, spring connections, spring leaf, etc.); a rotational and/or screw-type interlock, or any other.

They may also be coupled from a conductive protuberance on the electronics module that directly inserts into the adhesive conductive substrate that is making a connection with the surface of the skin.

In one embodiment, the electronics module element is attached above a point on the sensor element which is not adhesively attached to the user's skin. Due to the physical shape and placement design of adhesive components on the sensor element, the design provides for air flow and the ability to float with physical deformation of the skin without causing excessive pulling on the interface between the different sensor regions of the sensor element and the skin beneath them.

Figure 12A:
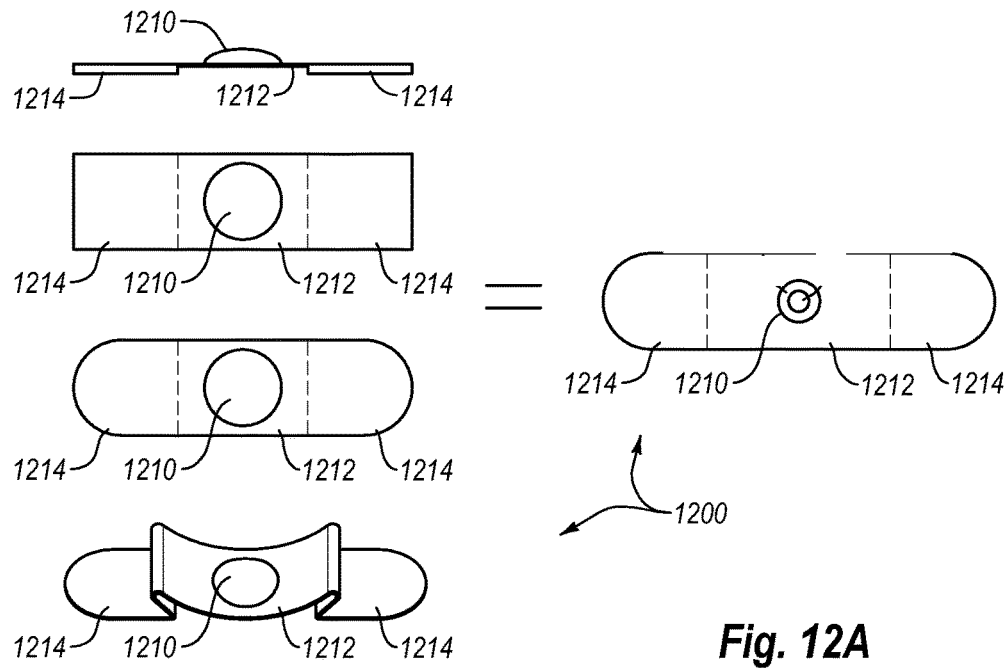
FIGS. 12A-12D include schematic representations of different embodiments of muscle sensor patches of a sensor system.

FIG. 12A shows a configuration of the sensor patch that includes a sensor element 1210 on a non-adhesive region 1212 and two adhesive regions 1214. The adhesive regions 1214 are on the ends of both of the lobes, with the non-adhesive region therebetween.

Figure 12B:
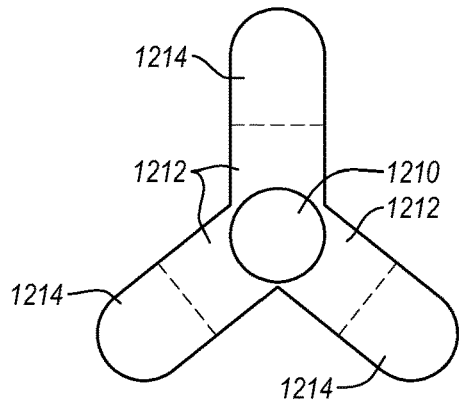
Figure 12C:
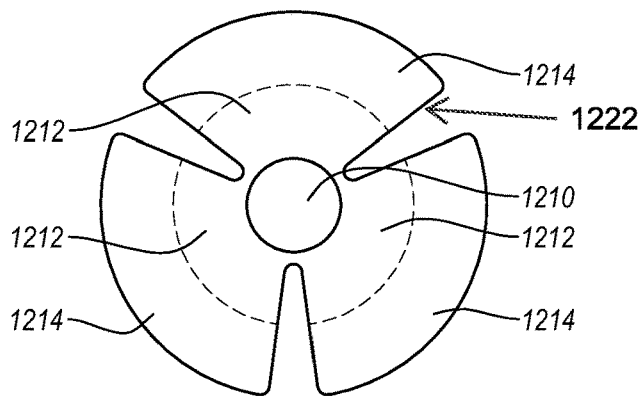
Figure 12D:
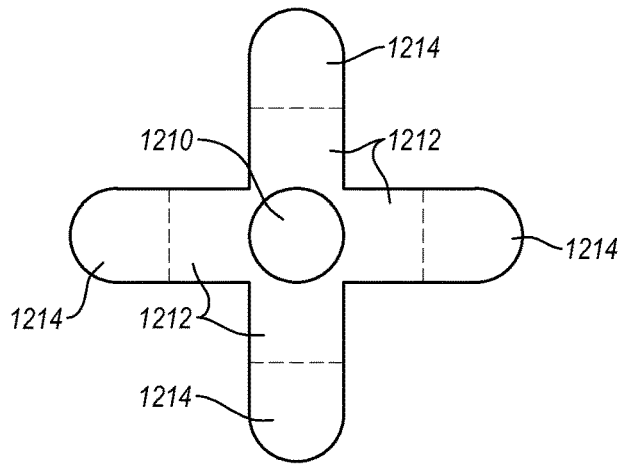

FIG. 12B shows one embodiment of the sensor patch that can be shaped as a propeller with three blades, which each have adhesive conductive regions 1214 near the extreme ends, and which have no adhesion present towards the middle 1210. FIG. 12C is similar to FIG. 12B but has four blades. This could be configured such that there is no adhesive or that the adhesive has been partially covered.

The sensor patch can include notches 1222 as shown in FIG. 12C in the adhesive bands to assist with flexibility. Also, the sensor patch can include absence of material and/or include molding or layer shaping may provide for additional flexibility in all 3 dimensions. For example, any flexible substrate may be used (e.g. conductive gel, cloth, flexPCB, etc.).

The electronic modules have sufficient flexibility such that while the sensor patch is worn, the microcontroller may be used to calculate relevant metrics and indices based on the raw data. The data can be transmitted and/or stored, and may be in raw or pre-formatted into relevant metrics.

The electronics modules can include at least one switch controlled by the microcontroller which is attached to resistors controlling the hardware amplification (e.g., if present in hardware form) and/or to the resistors controlling the filter settings. That can be performed in order to facilitate soft-switching between modes corresponding to ECG and EMG measurement.

In one embodiment, the electronics modules may include additional modules in order to function with different modalities to be measured in conduction with the electrophysiological signals of interest. These additional modalities help support and refine the gathered data by means of increasing the accuracy of the measurements, as well as allowing for secondary data gathering. These modalities may include examples such as accelerometer, temperature, impedance/GSR, GPS, user input/event markers, optical sensor, and audio sensor/microphone. However, these modalities may not be present on their own without a basic electrophysiology modality present as the primary modality (e.g., ECG, EMG, EEG, etc.).

In one embodiment, the sensor device can be configured to use a disposable coin-cell battery, a rechargeable battery such as an ultra-thin flexible Li-ion battery, or a micro power reclamation and storage unit that reclaims energy from the movement of the user that wears the sensor patch as the primary energy source.

In one embodiment, the flexible sensor patch is disposable. In one aspect, the peelable skin-contacting and adhering substrates can be disposable. The sensor patch can be partly disposable, or be either single use, or configured for a specified number of uses and/or number of hours.

In one embodiment, the flexible sensor patch may include a "silent record mode" in which the radio is disabled and data is saved to non-volatile memory, such as flash, microSD, or the like.

In one embodiment, the flexible sensor patch can transmit information to a mobile hub (e.g., described as mobile device) for feedback. The mobile hub can be configured as a watch, phone, gym equipment, smart phone, or other computing system having the proper software. The mobile hub can be configured with software into a mobile recording device without feedback, such as a SB stick with recording ability, to an earpiece enabled for audio-only feedback, or to a computer.

The inventive muscle sensor patches are completely flexible in all three dimensions to accommodate the movement of skin during a muscle activity. As such, the patches can have a relatively small thickness, which thickness can range from about 3 mm to about 5 mm, from about 5 mm to about 7 mm, or from about 7 mm to about 10 mm Each peelable adhesive substrate can have a thickness from about 1 mm to about 3 mm, from about 1.5 mm to about 2.75 mm or from about 2 mm to about 2.25 mm The skin-contacting surface can have a dimension, such as length or width, from about 1 cm to about 1.2 cm, from about 2 cm to about 5 cm, or from about 5 cm to about 10 cm. A preferred embodiment of the skin sensing patch includes the thickness to be about 5 mm, the width to be about 5 cm, the length to be about 5 cm and the shape to be a roughly circular.

The system may interact with other systems by means of the Internet. This could be facilitated automatically as to enable user-to-user, user-to-group, or group-to-group comparisons. This may be part of a social networking environment that includes user interaction. The mobile hub and/or base station can be operably coupled with one or more database computing systems for these comparisons.

In one embodiment, the present invention can include a system for monitoring muscle data. The system can include: one or more fully flexible sensor patches having one or more sensor modules configured to sense muscle data, one or more data processing modules, or more transmitter modules configured to transmit the muscle data, and a microcontroller configured to control the modules on one patch side and an adhesive layer on the other patch side, wherein fully flexible includes bending in all three dimensions with respect to the sensor elements; a wearable mobile hub having one or more of a receiver, transmitter, and/or transceiver module configured to be operably coupled with the one or more sensor patches so as to receive muscle data therefrom and a muscle data processing unit configured to process the received muscle data, and one or more user feedback interfaces configured to provide processed muscle data to the one or more user feedback interfaces; and a base station configured for receiving, storing, and analyzing the muscle data for one subject received from the mobile hub in comparison with one or more other subjects.

In one embodiment, the system can include each fully flexible sensor patch can have one or more active sensing elements and a one or more reference sensing element operably coupled over one or more channels. Alternatively, the system can include each fully flexible sensor patch having only a single active sensing element and/or a single reference sensing element configured to be operably coupled over one or more channels with the active sensing elements and/or reference sensing elements of other fully flexible sensor patches. In another alternative, the system can include each fully flexible sensor patch operably coupled over one or more channels to at least one other fully flexible sensor patch. In yet another alternative, the system can include each fully flexible sensor patch include one active sensor operably coupled to two other active sensors over two different channels. In another alternative, the system can include each fully flexible sensor patch including one or more sets of two operably coupled active sensors over independent channels and including one or more references. In one example, the sensor modules can include a sEMG module and/or an ECG module.

In one embodiment, the sensor patches can be configured to include sensor patch pairs. The patch pairs are configured to work together to provide data to the mobile hub. The patch pairs can use one patch as being active with one or more active sensors and optionally also having a reference sensor. Alternatively, the active sensors can be on one patch with the reference sensors on the other patch. In another alternative, both patches of the patch pairs can have one or more active sensors and one or more reference sensors. The patch pairs can be operably coupled by wire or wireless. The operably coupling can arise from both patches of the patch pair providing data to the mobile hub.

In one embodiment, the flexible sensor patches or patch pairs data can be selected from electrocardiography (ECG), electroencephalography (EEG), electrocorticography (ECoG), electromyography (EMG), electrooculography (EOG), electroretinography (ERG), electroantennography (EAG), and audiology data, and wherein the sensor elements are configured to measure one or more of the data. In a specific example, the sensor patches are configured for skeletal muscles (EMG). In another specific example, the sensor patches can be configured for the heart muscle (ECG).

The system can include a remote computing system having a database of electrophysiology data for a plurality of subjects. The data can be selected from electrocardiography (ECG), electroencephalography (EEG), electrocorticography (ECoG), electromyography (EMG), electrooculography (EOG), electroretinography (ERG), electroantennography (EAG), and audiology data, and wherein the sensor elements are configured to measure one or more of the data.

In one embodiment, the mobile hub is configured as a standalone computing device having data processing capabilities of a base station such that the mobile hub is capable of implementing base station function at unlimited distance from the base station.

In one embodiment, the side of the patch having the adhesive layer can include a skin-contacting surface partitioned into one or more conductive regions and one or more non-conductive regions, the one or more conductive regions being operably coupled to the one or more sensor modules. The conductive region can be less adhesive than the non-conductive region. The conductive region can be non-adhesive. The non-conductive region can be located as a border around the conductive region.

In one embodiment, the one or more sensor patches can include two or more peelable adhesive substrates containing the adhesive layer in a stack, each peelable adhesive substrate having a skin-contacting surface when a surface of the stack. The sensor patches can also include a protective pouch enclosing the sensor elements to a fully flexible sensor element substrate opposite of the peelable adhesive substrates.

In one embodiment, a first fully flexible sensor patch having first and second active sensing elements and a first reference sensing element. A second fully flexible sensor patch can have second and third active sensing elements and a second reference sensing element.

In one embodiment, the system can include an audible user feedback device operably coupled with the mobile hub, which audible user feedback device includes an adhesive surface and is adapted to be worn behind an ear.

In one embodiment, the mobile hub can be configured to be worn in a shoe or is part of the shoe.

In one embodiment, the sensor patch can include: sEMG and/or ECG modules in operably coupled with one or more of a high pass filter, low-pass filter, band-pass filter, one or more notch filters, a RMS calculation (Root Mean Square) unit, and/or a data smoothing unit; an amplifier in operably coupled with the microcontroller; a wireless transmitter operably coupled with the microcontroller; and the microcontroller having an EMG mode and an ECG mode.

In one embodiment, the system can also include an accelerometer module, a GPS module, a temperature module, an impedance module, a GSR module, and/or an EEG module. The system can also include a heel pressure sensor device having a pressure sensor module and a transmitter module.

In one embodiment, each sensor patch can include a module enclosure, a porous absorbing substrate and a porous wicking substrate. In one embodiment, the present invention can include a method of muscle performance assessment. The method can include: providing the muscle assessment system as described herein; applying one or more fully flexible sensor patches to skin of a subject so as to be operably coupled with one or more muscle; operably coupling the one or more sensor patches to the mobile hub; recording muscle data with the one or more patches; transmitting the muscle data from the one or more patches to the mobile hub; analyzing the muscle data with the mobile hub; providing the analyzed muscle data to the subject; providing the analyzed muscle data to the base station; obtaining muscle data from one or more other subjects; comparing the muscle data of the subject with muscle data from the one or more other subjects; and providing the compared data to the subject.

In one embodiment, the method can further include: removing the sensor patch from the skin; peeling an adhesive layer from the patch so as to expose a fresh skin-adhering surface; and applying the fresh skin-adhering surface to the skin of the subject.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The present disclosure is to be limited only by the terms of the appended claims, along with the full scope of equivalents to which such claims are entitled. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems from desktop computing systems, portable computing systems, tablet computing systems, hand-held computing systems as well as network elements, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Figure 15:
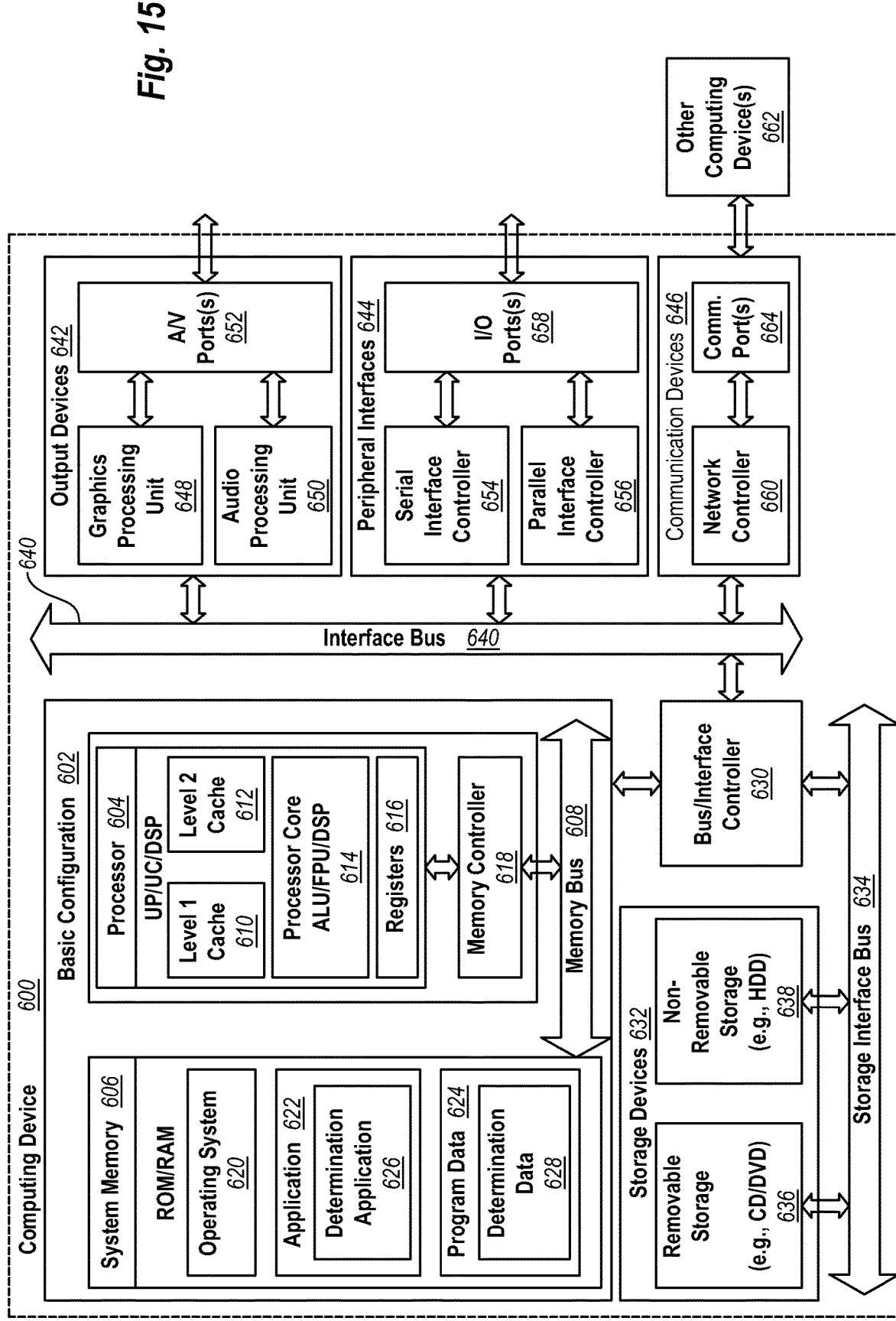
FIG. 15 includes a schematic representation of a computing device in accordance with the invention described herein.

FIG. 15 shows an example computing device 600 that is arranged to perform any of the computing methods described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including but not limited to a microprocessor (μP), a microcontroller (μC), a digital signal processor (DSP), or any combination thereof. Processor 604 may include one more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations memory controller 618 may be an internal part of processor 604.

Depending on the desired configuration, system memory 606 may be of any type including but not limited to volatile memory (such as RAM), non-volatile memory (such as ROM, flash memory, etc.) or any combination thereof. System memory 606 may include an operating system 620, one or more applications 622, and program data 624. Application 622 may include a determination application 626 that is arranged to perform the functions as described herein including those described with respect to methods described herein. Program Data 624 may include determination information 628 that may be useful for analyzing the contamination characteristics provided by the sensor unit 240. In some embodiments, application 622 may be arranged to operate with program data 624 on operating system 620 such that the work performed by untrusted computing nodes can be verified as described herein. This described basic configuration 602 is illustrated in FIG. 15 by those components within the inner dashed line.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the term "module" or "component" can refer to software objects or routines that execute on the computing system. The different components, modules, engines, and services described herein may be implemented as objects or processes that execute on the computing system (e.g., as separate threads). While the system and methods described herein are preferably implemented in software, implementations in hardware or a combination of software and hardware are also possible and contemplated. In this description, a "computing entity" may be any computing system as previously defined herein, or any module or combination of modulates running on a computing system.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above.

Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

What is claimed is:

1. A sensor patch comprising:
   a first active sensor element including a surface electromyography (sEMG) muscle sensor module configured to sense muscle data;
   a microcontroller configured to control the muscle sensor module;
   a data processing module configured to process the sensed muscle data;
   a transmitter module configured to transmit the processed muscle data;
   a first lobe including a first fully flexible skin-contacting adhesive portion of the sensor patch being disposed at an outer portion of the sensor patch;
   a second lobe including a second fully flexible skin-contacting adhesive portion of the sensor patch disposed at an outer portion of the sensor patch;
   the first skin-contacting adhesive portion including:
   a first adhesive layer for adhering the corresponding first lobe to the skin of a user;
   the second skin-contacting adhesive portion including:
   a second adhesive layer for adhering the corresponding second lobe to the skin of a user; and an inner non-adhesive portion of the sensor patch being disposed at an inner portion of the sensor patch, the inner non-adhesive portion separating the first and second skin-contacting adhesive portions having the first and second adhesive layers, wherein the sEMG muscle sensor module is disposed on, or at least partially within, the non-adhesive portion of the sensor patch for gathering sEMG data from the muscle of a user, wherein:

the sEMG muscle sensor module is located at the inner non-adhesive portion of the sensor patch;

the inner non-adhesive portion of the sensor patch is only partially surrounded by adhesive portions for adhering to the skin of the user, the inner non-adhesive portion being fully flexible with six-degrees of freedom relative to the first and second lobes; and the first and second lobes are flexible with six-degrees of freedom relative to the inner non-adhesive portion of the sensor patch and the first and second lobes increase in width as they extend from the inner non-adhesive portion of the sensor patch.

2. A sensor patch according to claim 1, further comprising:

a third lobe including a third fully flexible skin-contacting adhesive portion of the sensor patch disposed at an outer portion of the sensor patch;

the third skin-contacting adhesive portion including:

a third adhesive layer for adhering the corresponding third lobe to the skin of the user; and wherein the non-adhesive portion entirely separates the first, second and third adhesive layers across a width of the sensor patch.

* * * * *